(12) United States Patent
Forrest

(10) Patent No.: US 8,308,690 B2
(45) Date of Patent: Nov. 13, 2012

(54) DEVICE AND METHOD TREATMENT OR EVACUATION OF INTERVERTEBRAL DISC

(76) Inventor: Leonard Edward Forrest, Mt. Pleasant, SC (US)

( * ) Notice: Subject to any disclaimer, the term of this patent is extended or adjusted under 35 U.S.C. 154(b) by 0 days.

(21) Appl. No.: 13/042,984

(22) Filed: Mar. 8, 2011

(65) Prior Publication Data
US 2011/0190753 A1    Aug. 4, 2011

(51) Int. Cl.
*A61M 5/178* (2006.01)
(52) U.S. Cl. .................................. 604/164.11
(58) Field of Classification Search ............. 604/164.11
See application file for complete search history.

(56) References Cited

U.S. PATENT DOCUMENTS

| | | |
|---|---|---|
| 5,221,253 A | 6/1993 | Coll |
| 5,292,330 A | 3/1994 | Shutt |
| 5,980,504 A | 11/1999 | Sharkey et al. |
| 6,007,570 A | 12/1999 | Sharkey et al. |
| 6,073,051 A | 6/2000 | Sharkey et al. |
| 6,095,149 A | 8/2000 | Sharkey et al. |
| 6,122,549 A | 9/2000 | Sharkey et al. |
| 6,245,054 B1 | 6/2001 | Fuimaono et al. |
| 6,258,086 B1 * | 7/2001 | Ashley et al. .................... 606/41 |
| 6,261,311 B1 | 7/2001 | Sharkey et al. |
| 6,283,960 B1 | 9/2001 | Ashley |
| 6,409,727 B1 | 6/2002 | Bales et al. |
| 6,517,568 B1 | 2/2003 | Sharkey et al. |
| 6,547,810 B1 | 4/2003 | Sharkey et al. |
| 6,562,033 B2 | 5/2003 | Shah et al. |
| 6,595,959 B1 | 7/2003 | Stratienko |
| 6,602,248 B1 | 8/2003 | Sharps |
| 6,604,003 B2 | 8/2003 | Fredricks et al. |
| 6,638,276 B2 | 10/2003 | Sharkey et al. |
| 6,726,685 B2 | 4/2004 | To et al. |
| 6,733,496 B2 | 5/2004 | Sharkey et al. |
| 6,821,276 B2 | 11/2004 | Lambrecht et al. |
| 6,832,997 B2 | 12/2004 | Uchida et al. |
| 2001/0031963 A1 | 10/2001 | Sharkey et al. |
| 2002/0022830 A1 | 2/2002 | Sharkey et al. |
| 2002/0082585 A1 | 6/2002 | Carroll |
| 2003/0130712 A1 | 7/2003 | Smits |
| 2003/0181964 A1 | 9/2003 | Sharkey et al. |
| 2003/0199960 A1 | 10/2003 | Paskar |
| 2003/0225331 A1 * | 12/2003 | Diederich et al. ............ 600/437 |
| 2004/0015215 A1 | 1/2004 | Fredricks et al. |
| 2004/0015218 A1 | 1/2004 | Finch et al. |
| 2004/0083002 A1 | 4/2004 | Belef et al. |
| 2004/0087994 A1 | 5/2004 | Suddaby |

(Continued)

FOREIGN PATENT DOCUMENTS

WO         9742996 A1    11/1997

(Continued)

*Primary Examiner* — Nicholas Lucchesi
*Assistant Examiner* — Jason Flick
(74) *Attorney, Agent, or Firm* — B. Craig Killough

(57) ABSTRACT

A method of positioning an arcuate device against the inner walls of the disc, and particularly on the posterior and postero-lateral portions of the inner annulus of the disc. The arcuate device retains its predetermined arcuate shape when no pressure or force is applied to the catheter. In an embodiment, an arcuate cutter is used to remove tissue from the inner annulus of the disc. In another embodiment an arcuate device is used to progressively remove material from the interior of the mammalian intervertebral disc. In yet another embodiment, an arcuate device is used to remove the entire intervertebral disc and place supports to maintain a disc space.

56 Claims, 21 Drawing Sheets

U.S. PATENT DOCUMENTS

| | | |
|---|---|---|
| 2004/0102824 A1 | 5/2004 | Sharkey et al. |
| 2004/0111136 A1 | 6/2004 | Sharkey et al. |
| 2004/0111137 A1 | 6/2004 | Sharkey et al. |
| 2004/0127963 A1 | 7/2004 | Uchida et al. |
| 2004/0193045 A1 | 9/2004 | Scarborough et al. |

FOREIGN PATENT DOCUMENTS

| | | |
|---|---|---|
| WO | 0105330 A1 | 1/2001 |
| WO | 02-11635 | 2/2002 |
| WO | 02-098314 | 12/2002 |

* cited by examiner

DEVICE AND METHOD TREATMENT OR EVACUATION OF INTERVERTEBRAL DISC

Applicant claims priority upon U.S. application Ser. No. 11/972,815 filed Jan. 11, 2008, which claims priority upon U.S. application Ser. No. 11/112,475 filed Apr. 23, 2005, now U.S. Pat. No. 7,322,962, which benefit is claimed hereby, and which claimed priority on the following Provisional Applications.

Applicant claims the benefit of U.S. Provisional Application Ser. No. 60/564,838 filed Apr. 23, 2004.

Applicant claims the benefit of U.S. Provisional Application Ser. No. 60/572,930 filed May 20, 2004.

Applicant claims the benefit of U.S. Provisional Application Ser. No. 60/586,627 filed Jul. 9, 2004.

Applicant claims the benefit of U.S. Provisional Application Ser. No. 60/588,582 filed Jul. 16, 2004.

Applicant claims the benefit of U.S. Provisional Application Ser. No. 60/588,587 filed Jul. 16, 2004.

FIELD OF INVENTION

This invention and method relate to the treatment or evacuation of an intervertebral disc.

BACKGROUND OF THE INVENTION

The intervertebral disc is comprised of an outer annulus fibrosis and an internal nucleus pulposus. The healthy annulus is comprised of 10-20 lamellae forming a concentric ring of collagen and elastic fibers around the nucleus while the healthy nucleus pulposus is ovoid and composed of a gelatinous mucoprotein within the confines of the annulus fibrosis.

In the healthy normal disc, the annulus is thick and the internal wall is strong and without significant defects. Aging and trauma cause multiple and varied defects of the annulus as well as changes in the nucleus. These defects are a source of pain for many individuals. It is widely accepted that the defects which actually do cause pain are either posterior or postero-lateral. By far, it is most common that symptomatic defects are posterior and/or unilateral postero-lateral. Symptomatic defects which are posterior and bilateral postero-lateral certainly do exist but are definitely less common. On the other hand, degenerative changes with defects along the inner annular wall can be found commonly in various other segments of the inner annular wall (anteriorally, antero-laterally on either or both sides, and laterally on either or both sides. These defects are understood to be asymptomatic, but nevertheless are common.

Radiofrequency is used to treat internal intervertebral disc disruption. Forward pressure is applied to circumvent the nucleus adjacent to the inner annular wall, leverage with the forward pressure against the annular wall opposite to the portion attempting to be treated, or drive through the annular tissue which is intended to be treated.

The catheter is advanced around the inside of the nucleus pulposus adjacent to the inner annular wall. However, in the spectrum of discs requiring treatment, ideal discs are infrequently encountered. The result is that the tip of the catheter, even with a bent and/or capped tip gets caught in defects in the wall, making the advancement difficult or impossible. This frequently results in kinking of the catheter (which then typically must be removed), lodging into the defect (presumably worsening the defect), going through the annular wall (obviously creating a through and through defect in the annular wall and even potentially puncturing or damaging nerve or vascular structures), and ultimately making the intended treatment sub-optimal or even impossible. Additionally, in such situations there has been further damage caused to the disc by the catheter. The defects into which the catheter can inadvertently probe can be the defect, or defects, intended to be treated. Alternately, a defect in the anterior, antero-lateral, or lateral wall can equally be entered inadvertently and cause a disruption of the procedure. Degenerative disc walls commonly contain multiple such defects, as well as thinning of the wall, which are all too frequently penetrated.

SUMMARY OF THE INVENTION

The invention includes a method of positioning an S-shaped tool against inner annular walls of the disc, and particularly on the posterior and postero-lateral portions of the inner annulus of the disc, by arthroscopy. The apparatus used according to one method requires no forward tip pressure on the inner annular wall of a mammalian intervertebral disc. An arcuate and S-shaped tool such as a catheter is positioned against the inner annular wall of the disc, and particularly on the posterior and postero-lateral portions of the inner annulus of the disc, which are specifically the portions which need to be treated. The arcuate and S-shaped tool retains its predetermined arcuate and S-shape shape when no pressure or force is applied to the tool.

In another embodiment an arcuate and S-shaped device such as a sheath is used to progressively remove material from the interior of the mammalian intervertebral disc. In yet another embodiment, an arcuate and S-shaped tool device such as a sheath and catheter are used to remove the entire intervertebral disc and place supports to maintain a disc space.

DESCRIPTION OF PREFERRED EMBODIMENTS

Figure 1:
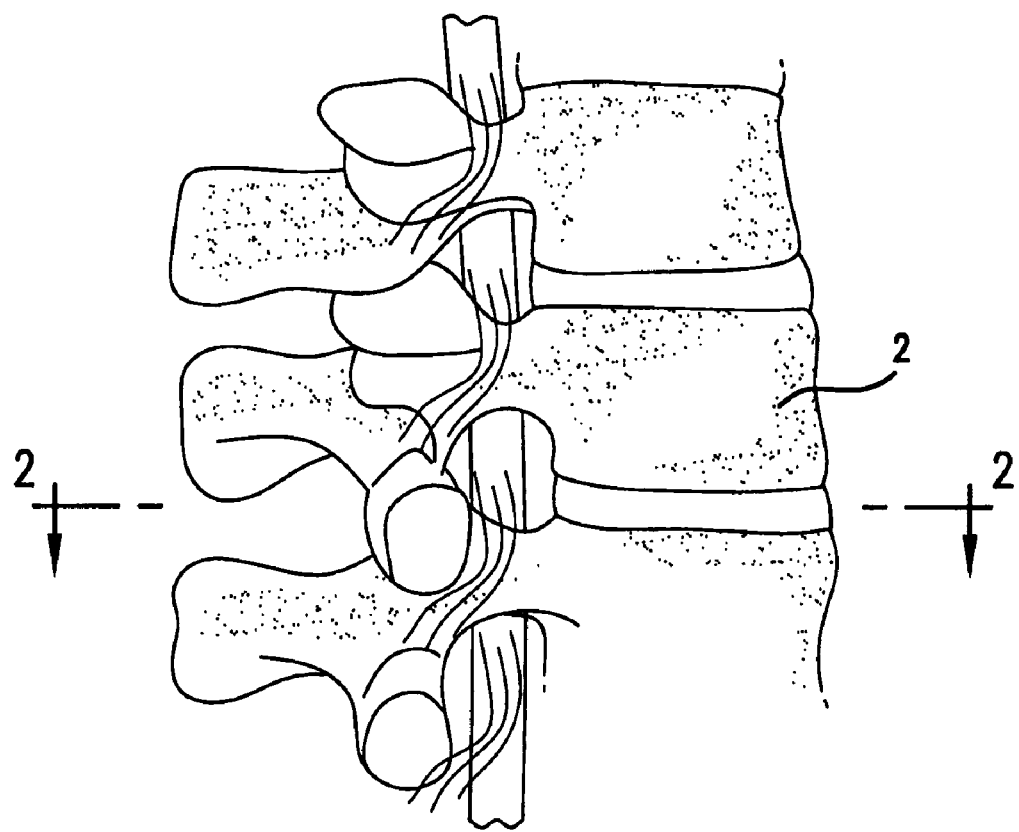
FIG. 1 shows a partial lateral view of a portion of a human spine.
Figure 2:
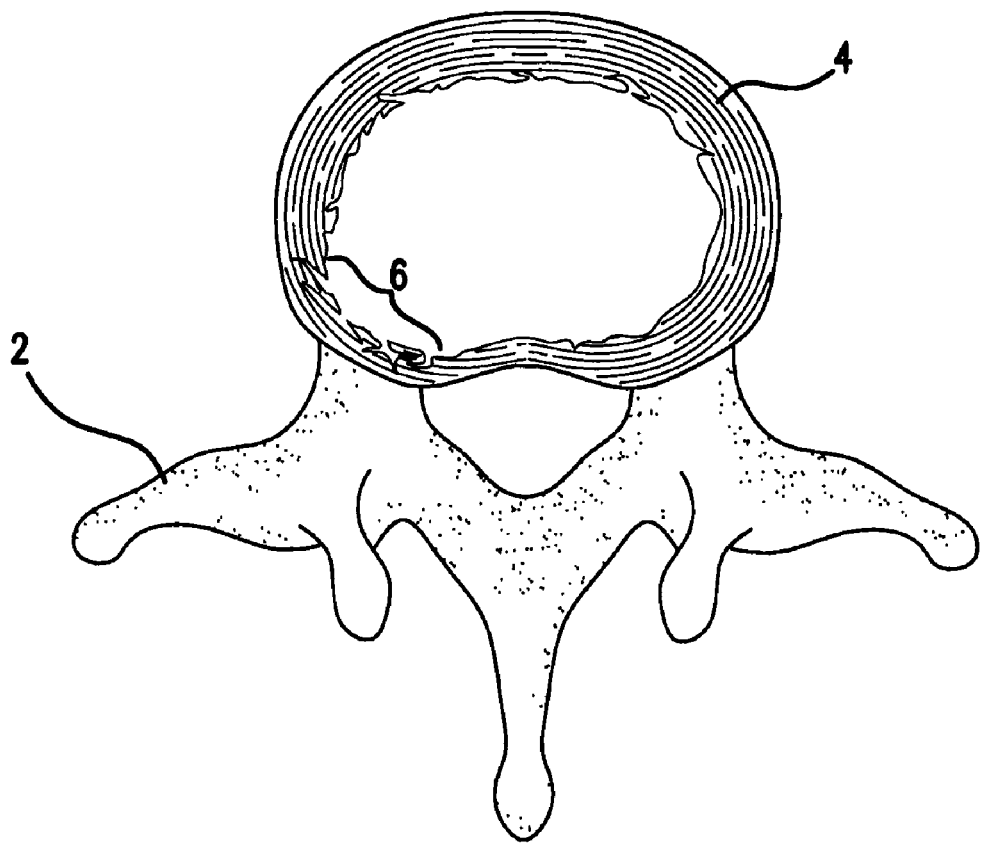
FIG. 2 is a sectioned view taken essentially along line 2-2 of FIG. 1.

Turning now to the drawing figures, FIG. 1 shows a partial view of a mammalian spine, and more particularly, a human spine 2. FIG. 2 is a sectioned view taken essentially along line 2-2 of FIG. 1, and shows an annular wall of a disc 4 of a human spine. The inner annular wall is rough, or jagged, due to trauma, aging and/or disease. Treatment of the portion of the disc labeled 6 is indicated due to its condition. Advancement of a catheter into the disc, and around the wall of the disc to the area to be treated is difficult, since the tip of the catheter is likely to engage the rough, jagged inner annular wall. The catheter is preferred to be laid against the portion of the disc intended to be treated, minimizing the course of the catheter within the disc, yet assuring good contact of the catheter with the portion of the disc to be treated. The angle of entry into the disc should be maximized to accommodate a spectrum of operative conditions and needle placements. The portion of the disc requiring treatment as contemplated in this embodiment is postero-lateral (one side or both), plus or minus a portion of the posterior wall. The route to the interior of the disc must be straight. For humans, the distance from the outer layer of skin to interior of the disc is approximately 12 to 30 centimeters, depending upon the size of the individual upon which the process is performed.

Figure 3:
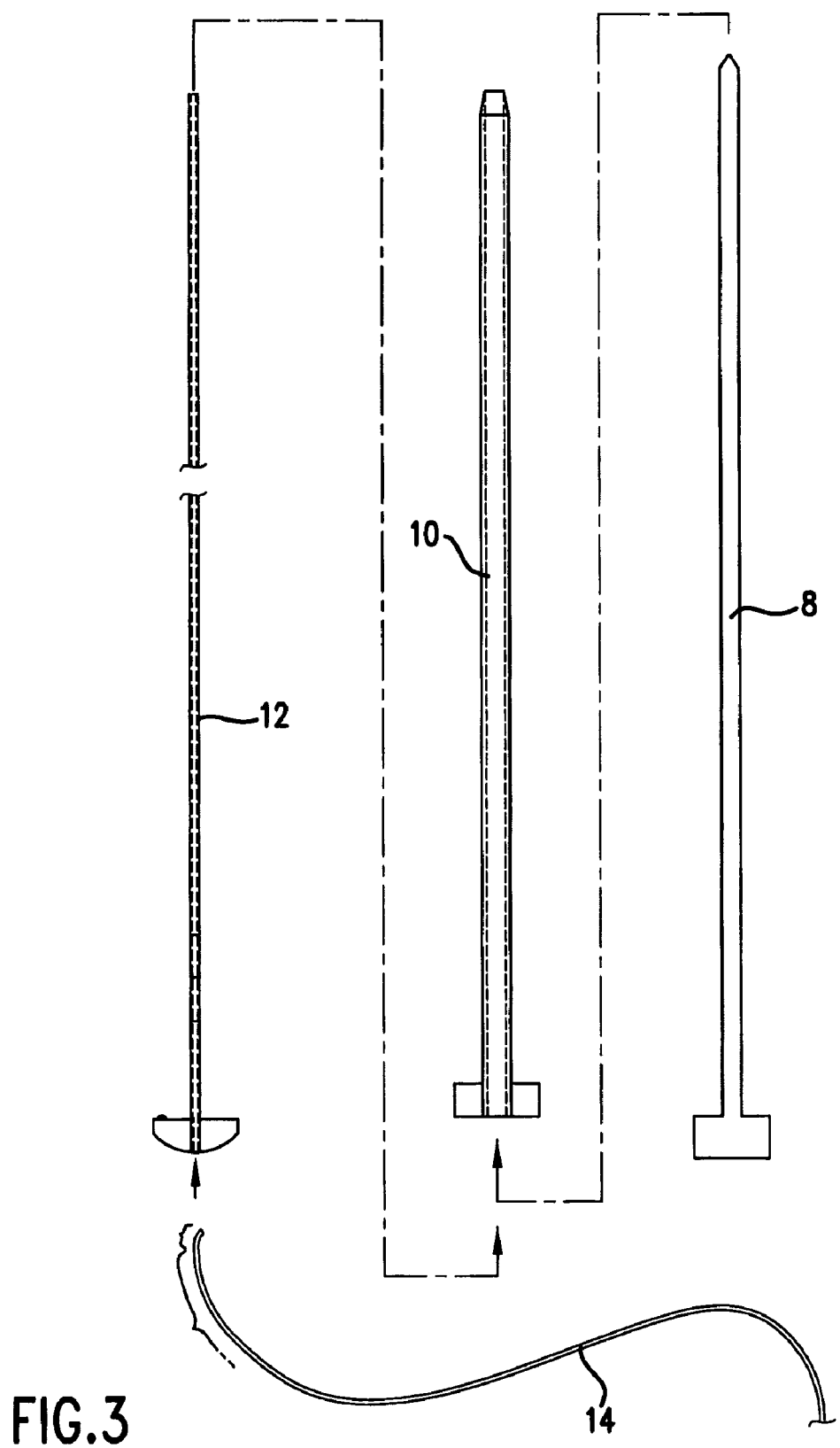
FIG. 3 is an exploded view showing the introducer needle, non-conductive sheath, stylet and catheter.

FIG. 3 shows the primary elements of the apparatus of the present invention. A stylet 8 is inserted into an introducer needle 10. A lumen in the form of a sheath 12 is subsequently inserted into the introducer needle, and a catheter 14 having a preformed S shape is advanced through the sheath. The lumen acts as a guide through which the S-shaped tool such as a catheter, is transported. The guide may take other forms that will assist transportation of the tool into the disc, such as a track or a wire that the tool engages. In one embodiment, the guide is part of the introducer needle, such as lumen therein. The introducer needle is preferred to be straight for ease of placement and due to the distance from the skin to the interior of the disc. The introducer will generally have a length in excess of 10 centimeters.

The stylet and introducer needle form a passage into the disc through the posterior wall of the disc on the side opposite that requiring treatment. The stylet is intended to keep the tissue from accumulating within the advancing introducer needle.

The introducer needle is advanced under fluoroscopic guidance lateral to the superior articular process. The annulus is punctured and the introducer needle may be advanced initially approximately one-third to one-half of the distance of the disc, as can be judged by operators skilled in performing such procedures.

Figure 4:
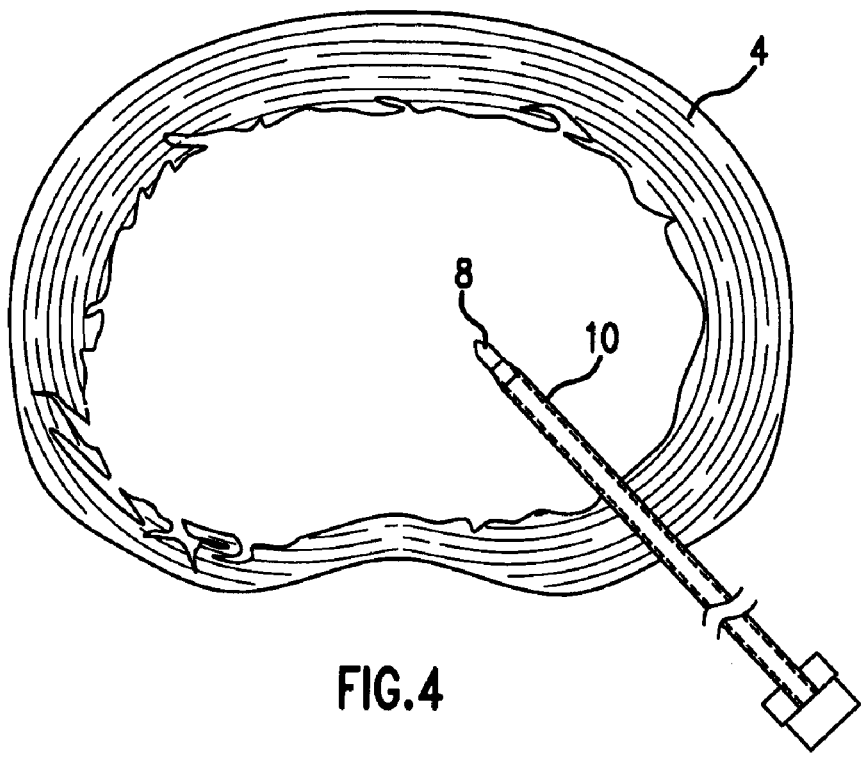
FIG. 4 shows the introducer needle with stylet in place and having penetrated the annular wall of the disc.
Figure 5:
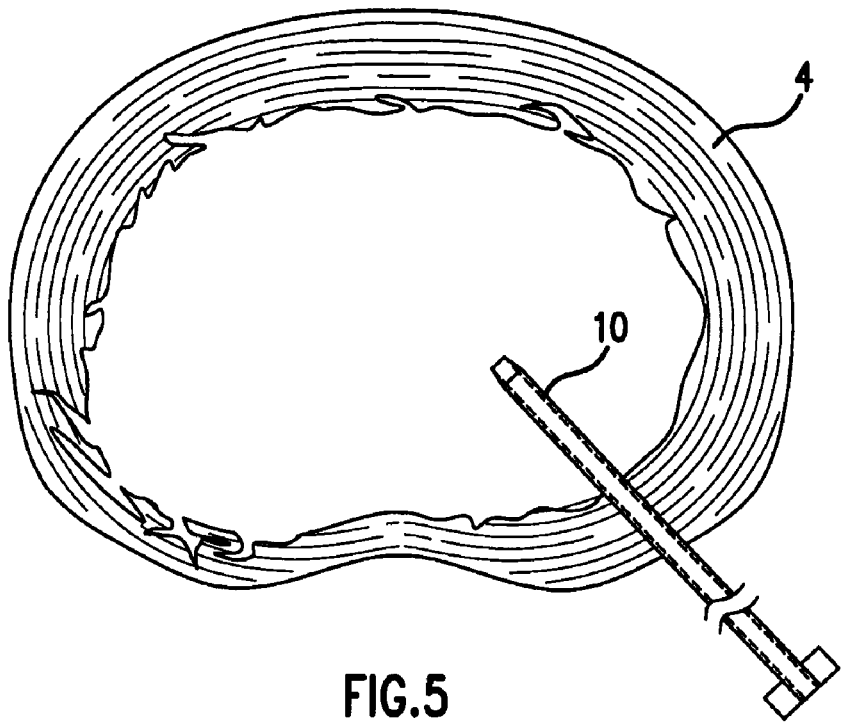
FIG. 5 shows the introducer needle with the stylet removed.

FIG. 4 shows the introducer needle with stylet in position. The sharp point of the stylet is driven through the wall of the disc, along with the introducer needle. The stylet is then removed. FIG. 5.

After the stylet and introducer needle pierce the annular wall of the disc and access the interior of the disc, the stylet is removed and is replaced with a lumen, which may be a sheath. A pre-formed, S-shaped catheter or other tool having memory retention properties is contained within the straight sheath. The straight sheath is inserted through the introducer needle for introduction into the disc. The catheter is straightened by the pressure from the walls of the sheath, but the catheter regains its S-shape as it exits the sheath. As shown in the drawings, the S-shape comprises two separate and distinct arcs.

The sheath locks into place at the external end of the introducer needle. When locked into place, the catheter sheath will protrude from the tip of the introducer needle. The sheath remains well contained within the disc nucleus and not in the proximity of the opposing annular wall but may be advanced or retracted as necessary for catheter positioning.

The sheath is preferred to be made of nonconductive material having thermal insulative properties sufficient to avoid undesired heating of tissues and structures outside of the disc, even if the heating portion of the catheter comes into close proximity or even contact with this sheath. The sheath may be straight, or slightly curved, and capable of advancing through the introducer needle once the stylet is removed. It has sufficient rigidity to maintain a portion of the catheter in a straight position while that portion of the catheter is in the sheath. The sheath is capable of externally locking at an upper portion into the introducer needle at the hub.

The non-conductive catheter sheath ensures that no inadvertent heating of the introducer needle occurs. Heating may cause significant unwanted damage to skin, subcutaneous tissue, fat, muscle, and even nerve.

Figure 6:
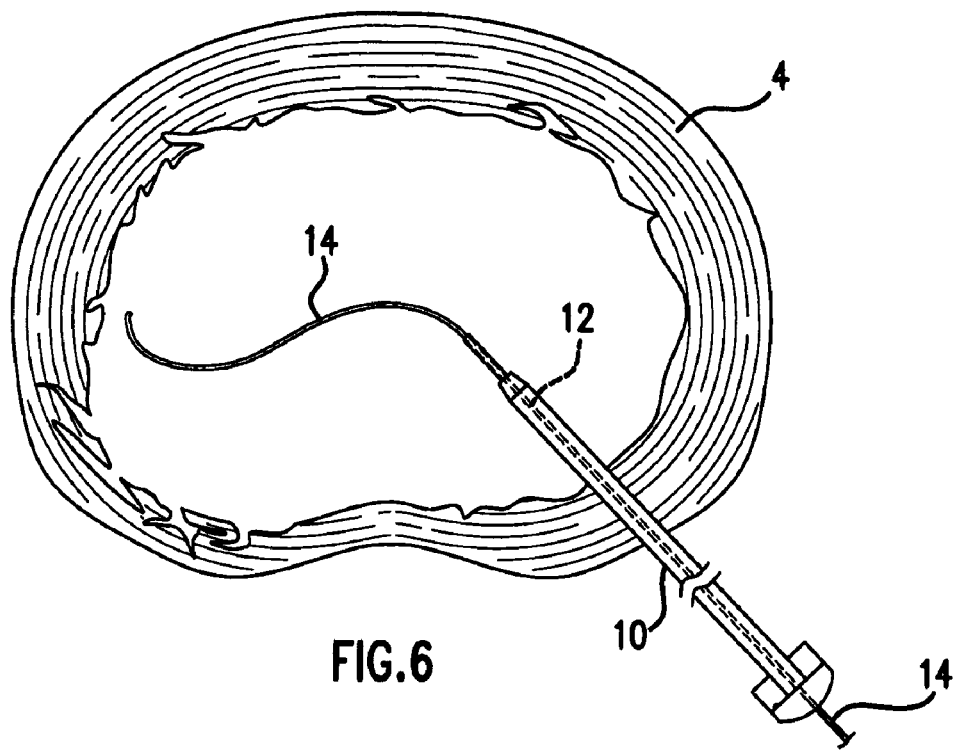
FIG. 6 shows the non-conductive sheath inserted into and through the introducer needle, with the S-shaped catheter advanced through the sheath.
Figure 7:
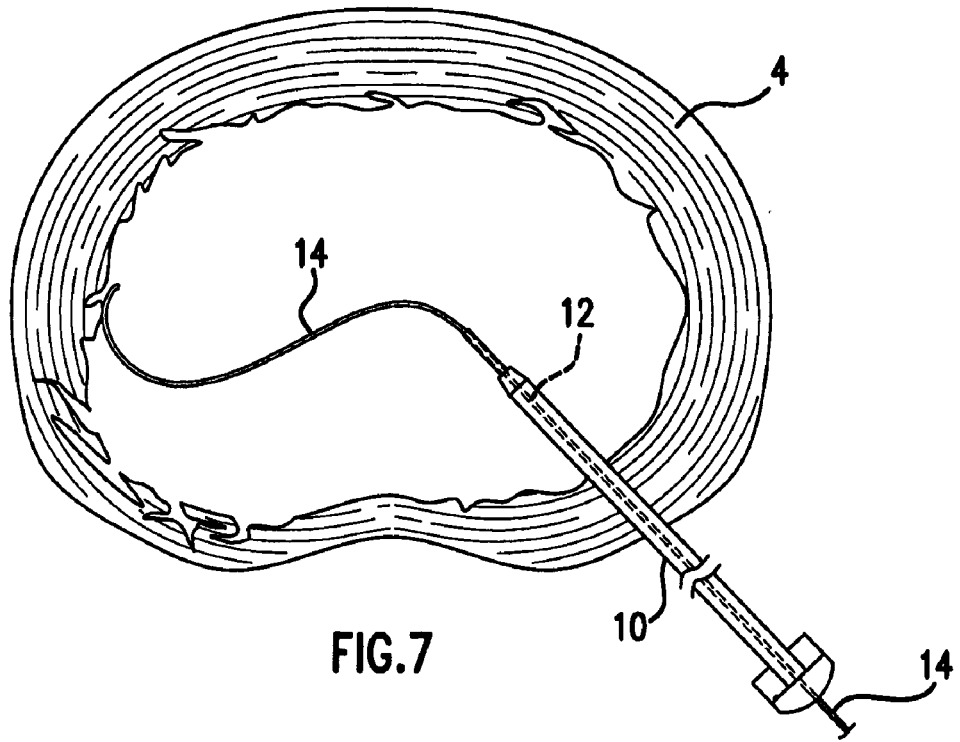
FIG. 7 shows the S-shaped catheter extended as required through the sheath.

The sheath is inserted into the lumen of the introducer needle, while the introducer needle remains in position within the disc as shown in FIG. 5. In FIG. 6, the catheter is advanced through the sheath. As the S-shaped catheter exits the sheath within the interior of the disc, the catheter, due to memory retention properties, and with no pressure applied, assumes its S-shape, with two separate and distinct arcs, as shown in FIG. 6. In FIG. 7, the catheter continues to advance and contacts the lateral inner annular wall of the side on which the postero-lateral wall is to be treated. Catheter advancement may be fluoroscopically monitored.

Figure 8:
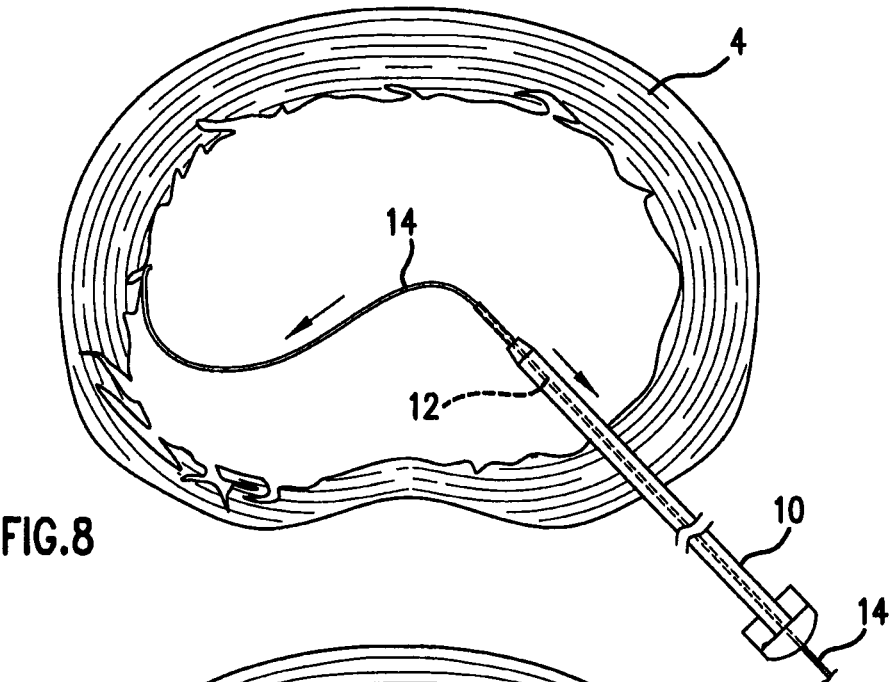
FIG. 8 demonstrates the introducer needle and sheath being retracted to position the catheter.

FIG. 8 demonstrates the introducer needle being retracted from the disc as the catheter is advanced. This combination of movements causes the catheter to move toward the postero-lateral and posterior wall which is the intended side of treatment. As shown, the introducer needle and sheath are retracted until the catheter is in position against the site to be treated. Positioning of the sheath and the catheter may be monitored fluoroscopically.

Figure 9:
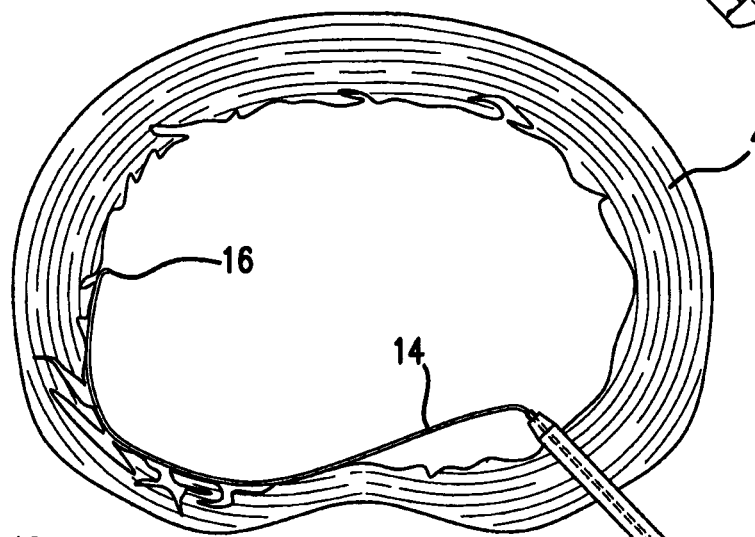
FIG. 9 shows the introducer needle and sheath retracted, and the catheter positioned against the inner annular wall defect.
Figure 10:
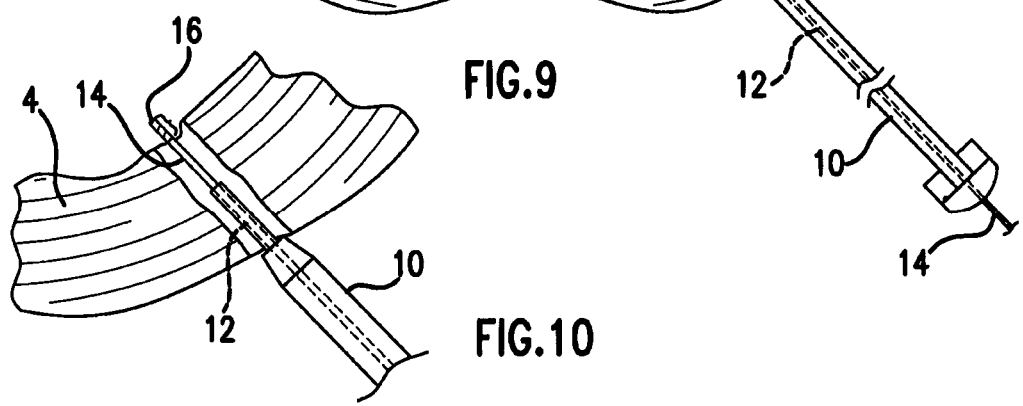
FIG. 10 demonstrates the device being withdrawn from the disc and the iatrogenically created defect being sealed.

As shown in FIG. 9, the introducer needle is retracted until the catheter rests against the lateral posterior wall to be treated. The lateral posterior wall to be treated is opposite the side of the posterior wall that the introducer needle has penetrated. Heat or radio frequency can be applied to the disc wall by means of the catheter. Other therapeutic procedures may be applied by use of an appropriate catheter. The catheter may then be retracted, and the introducer needle is retracted from the disc as shown in FIG. 10. Either the tip of this catheter can be differentially heated to seal the needle entry defect, or the S shaped catheter is removed and replaced with a straight catheter with a heating element at the tip. Heating of the tip as the needle-sheath-catheter complex is withdrawn seals the entry defect. Alternately, a catheter with a portal at the tip to inject a sealant of this entry defect may be used.

For needle positions between the extremes of acute and obtuse, the length of sheath versus disbursed catheter will determine the position at which the catheter tip will come into contact with the opposite lateral wall. Recognition of the goal of having the catheter contact the mid portion of the lateral wall of the side to be treated, and monitoring progress under fluoroscopy will facilitate ideal catheter placement.

The portion of the catheter intended to be within the disc has an S shape when no material pressure or force is applied to the catheter. The catheter may be formed of nitinol, which is sufficiently flexible to be advanced through a straight lumen or sheath, but will regain the preformed arcuate or S-shape when present within the interior of the disc. The catheter should also be sufficiently flexible to conform to the shape of the disc wall, such as the posterior wall of the inner disc, when positioned against the wall. FIG. 9.

The S-shaped catheter allows the physician to treat the posterior wall, and particularly the lateral posterior wall, of a defective disc without the necessity of first contacting the anterior wall with the catheter. The device and process prevent the end or tip of the catheter from catching or hanging against the rough interior annular wall, which may have many crevices that make it difficult to advance the catheter along the wall. The S-shaped catheter allows the catheter to be introduced into the interior of the disc, and then positioned by manipulation of the introducer needle and catheter, without subjecting the catheter to being snagged by defects in the disc. The S shape facilitates good contact of the catheter with the postero-lateral segment of the disc even if the angle of the needle entry is suboptimal. Additionally, the S shape retards the catheter traversing through any large segment of the interior of the disc which is typically filled with debris. This minimizes "shoveling" of the debris toward the segment of the inner annular wall to be treated. One skilled in the art will recognize that since the S-shape of the tool facilitates reaching the lateral wall portions and surfaces of the disc, which are the most difficult portions to reach, that the tool of this shape will reach remaining portions and surfaces of the disc.

Catheters may contain heating segments of various lengths. A final heating element, which is contained in each of these types of catheters, may be present directly at the tip, and is used for the spot sealing on exit from the inner annular wall. An additional embodiment has a straight catheter with a heating element at the tip.

On withdrawal of the catheter, the end or tip of the catheter straightens as it is exiting the annular wall. Spot heating at this position by tip 16 seals the defect that was created by the introducer and catheter.

Figure 11:
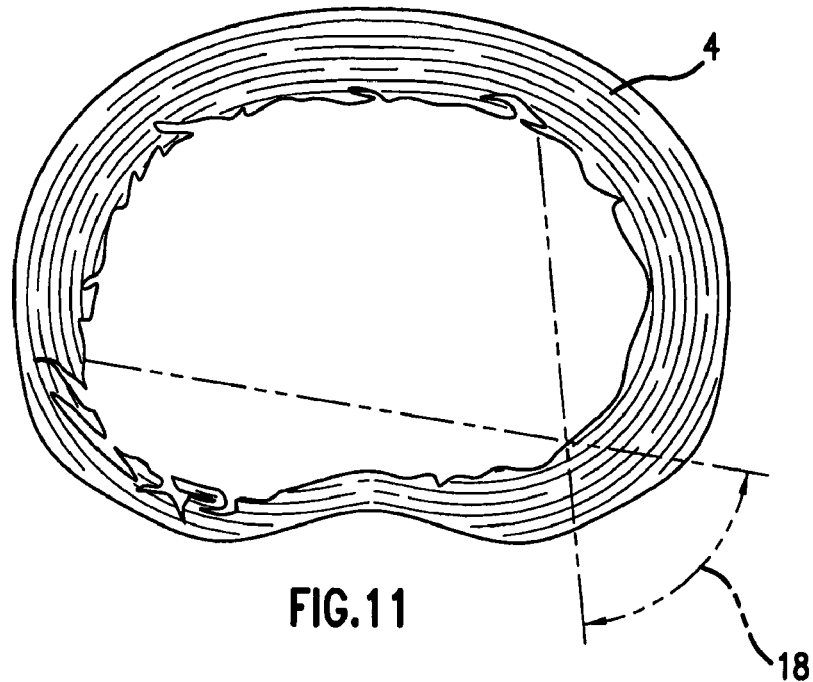
FIG. 11 demonstrates a range of permissive angles of insertion of the introducer needle relative to the disc.

FIG. 11 demonstrates an acceptable range of angles of needle insertion 18 when driving the introducer needle into the disc. The acceptable range of angles is within about 70 degrees, but is not less than forty five degrees. Due to the S shaped configuration of the catheter, a precise entry of the introducer needle is not required.

Figure 12:
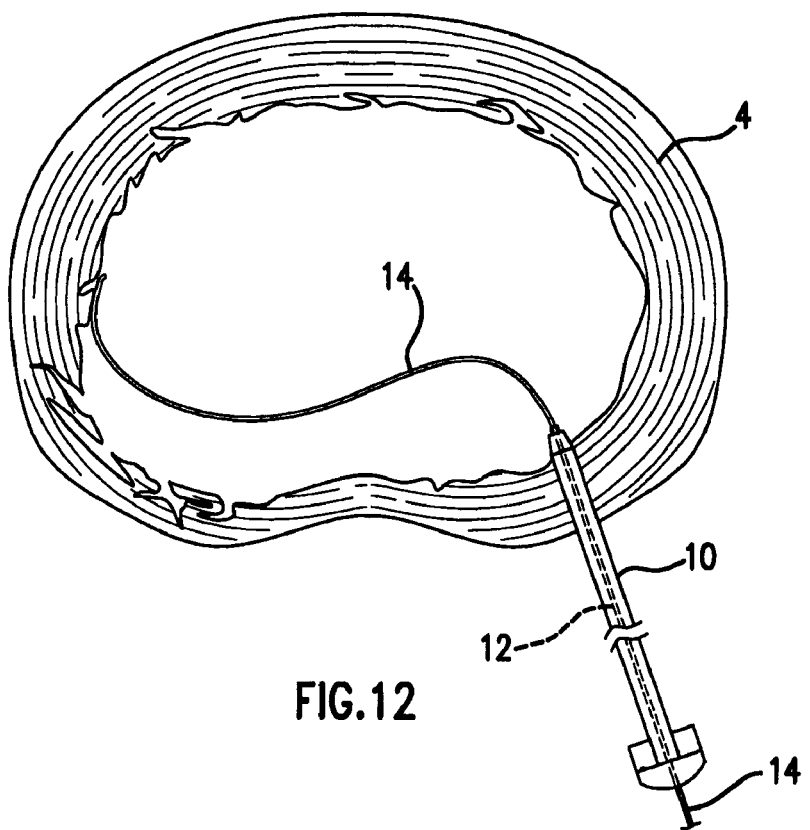
FIG. 12 demonstrates the introducer needle penetrating the annular wall at a different angle from that shown in FIGS. 4 through 10.
Figure 13:
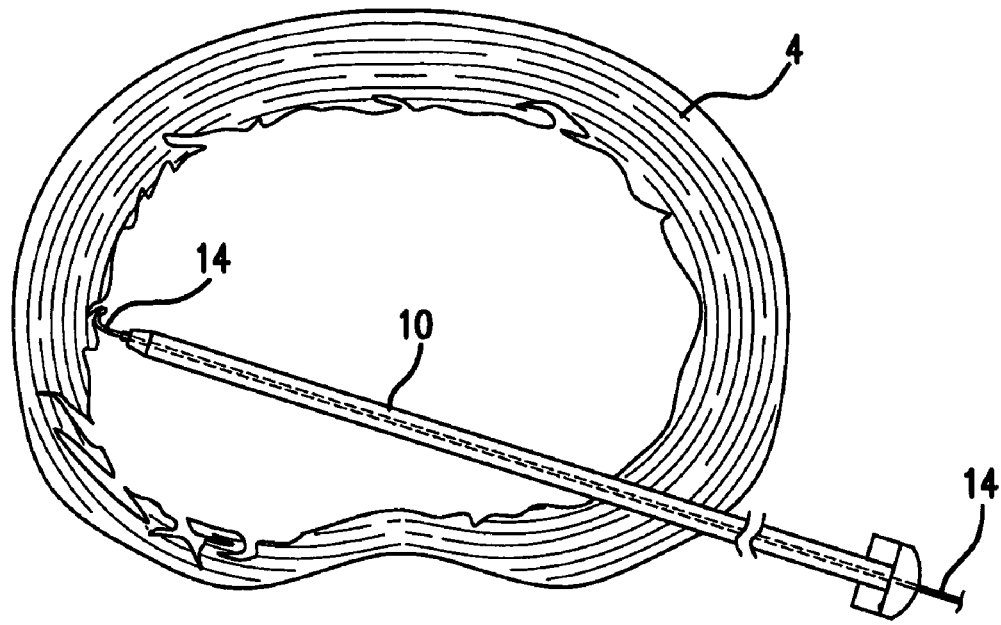
FIG. 13 demonstrates another angle of entry of the introducer needle into the disc.

As shown in FIG. 12, acceptable results are achieved with the S-shaped catheter used according to the novel method, even though the angle of needle insertion varies from that shown in FIG. 9. Likewise, the angle of needle insertion may be varied as shown in FIG. 13. The introducer needle may be withdrawn from the position shown in FIG. 13 to the interior, posterior annular wall, and S-shaped catheter is capable of being positioned against the lateral posterior wall of the disc by the method stated above.

Figure 14:
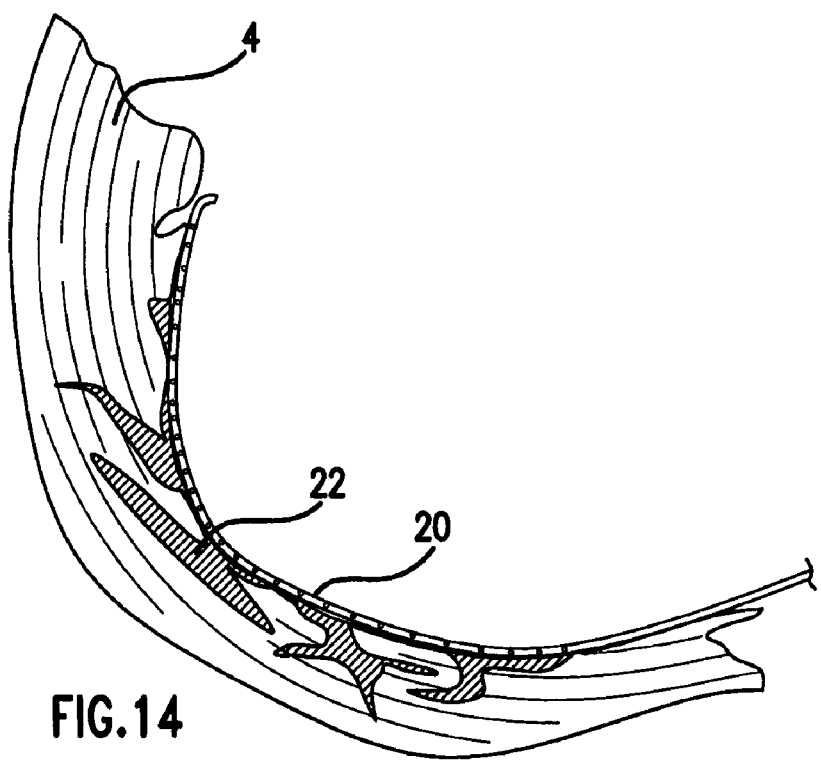
FIG. 14 demonstrates a catheter having multiple orifices therein through which materials may be dispensed.

The catheter may provide heat or radio frequency for the purpose of treatment of the disc. Other therapeutic applications may be used with the device and method. Further, a catheter 20 may have multiple orifices for the purpose of delivering materials such as adhesives, sealants or fillers into the disc. FIG. 14. A substance 22 may be injected through the catheter to the affected site to seal chemically, or otherwise, as opposed to thermally, defects including fissures and tears in the annular wall. Pressure manometery or fibro-optical viewing are also possible uses of this catheter system.

Figure 15:
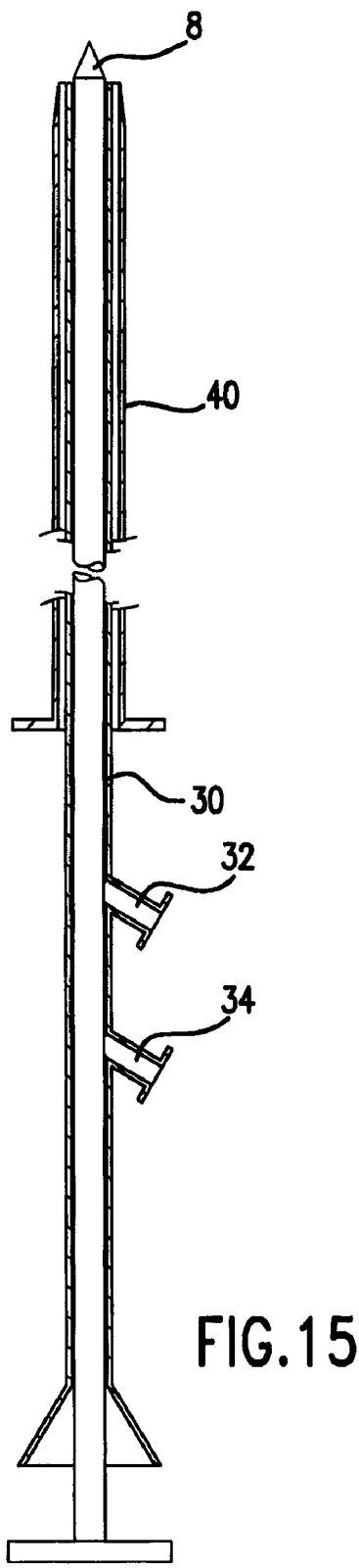
FIG. 15 is a sectioned view of an introducer needle inserted into a sheath having ports therein.
Figure 17:
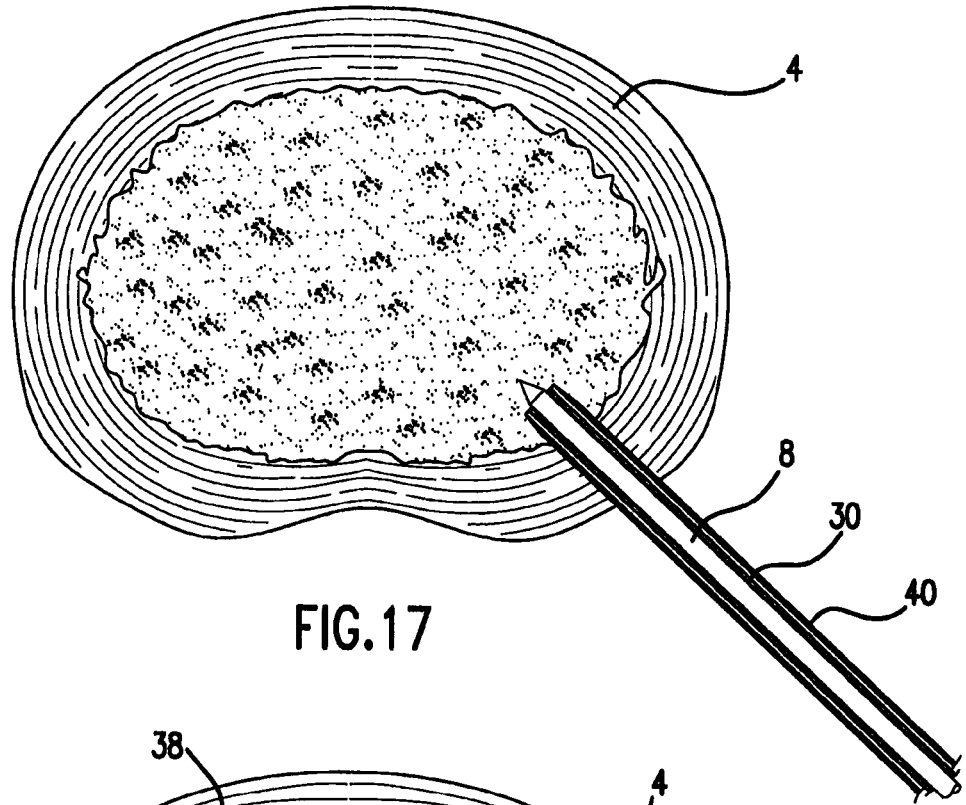
FIG. 17 demonstrates an introducer needle and stylet penetrating a disc.

FIG. 15 shows a second embodiment of the device, wherein the sheath has ports 32, 34 formed therein. The stylet is shown in position in the introducer needle of this embodiment. The stylet and introducer needle are used to access the interior annulus of the disc and shown in FIG. 17.

After entry into the disc, the stylet is withdrawn. The ports of the sheath may be used to insert materials into the disc, or remove materials from the disc. A vacuum may be applied to the ports for the purpose of removal of material.

Figure 18:
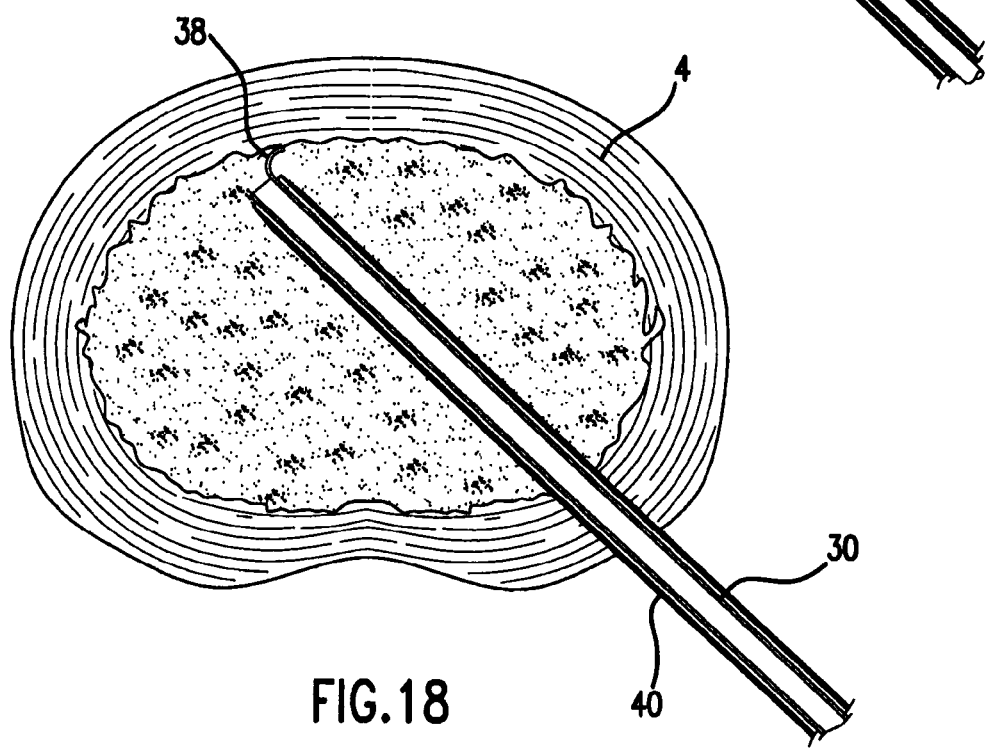
FIG. 18 demonstrates the flexible tip bending on contact with the inner annular wall.
Figure 19:
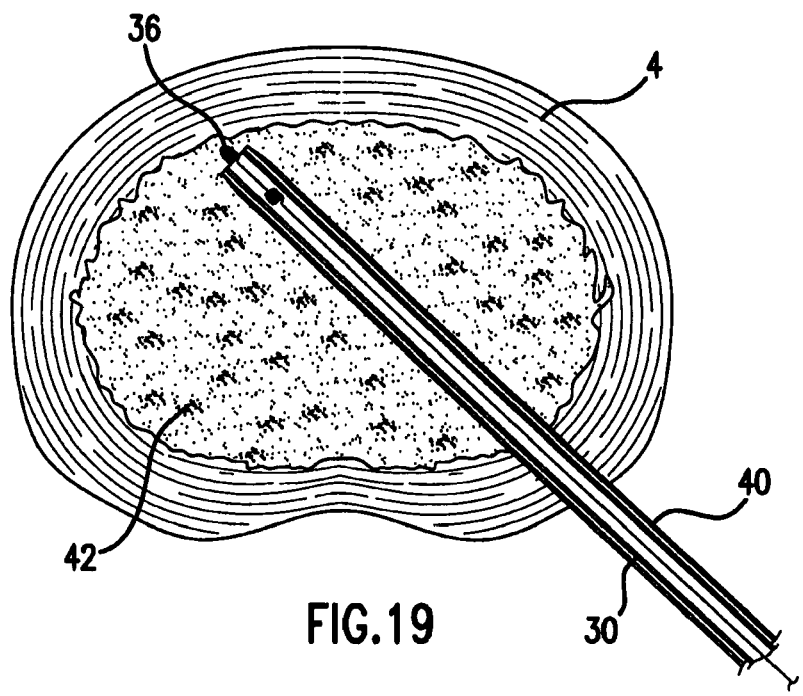
FIG. 19 demonstrates a cutter which may be used to remove material from the disc.

FIG. 18 shows a flexible deformable tip of the sheath. Deformation of the tip, which may be visualized fluoroscopically, defines hitting the inner annular wall. In one embodiment, 0.5 centimeters is sufficient protrusion of the sheath, such that it can be observed to bend when it contacts opposite inner annular wall. The bending of the tip of the sheath defines the limit of the inner annular wall immediately across from the entrance of the introducer needle complex into the disc. The limit of the inner annular wall opposite to the needle insertion may be defined when fluoroscopically viewed.

Figure 16:
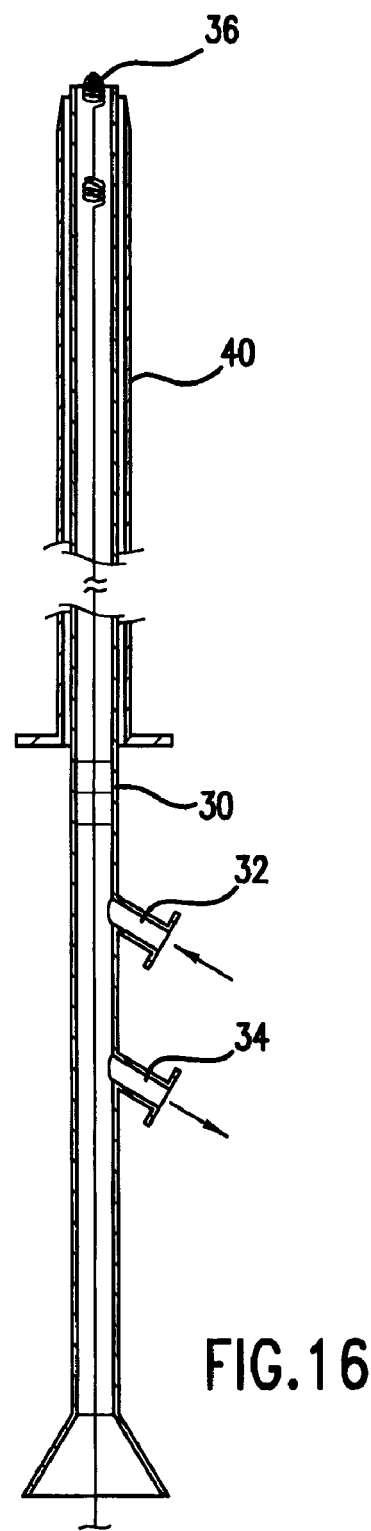
FIG. 16 is a sectioned view of an introducer needle having ports through which materials may be inserted into the disc, or from which materials may be removed, such as by vacuuming, and also showing a cutter therein.
Figure 20:
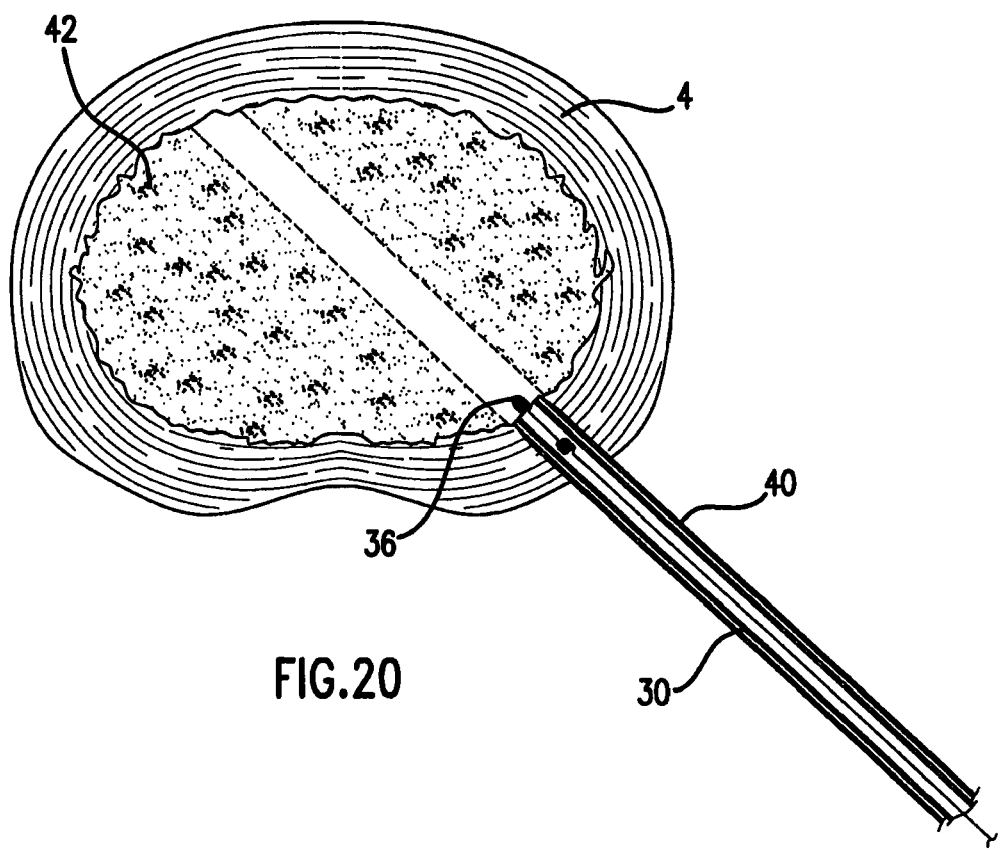
FIG. 20 demonstrates removal of a path of disc material using a cutter and a lavage/suction.

As shown in FIG. 16, a rotary cutter 36 is contained within the sheath. The rotary cutter is used to cut away material as the introducer needle is withdrawn. FIG. 20. Alternately, another type of cutter may be used.

When the introducer needle, sheath and cutter complex are in the nucleus, the tip of the flexible sheath is advanced by external manipulation such that it protrudes from the introducer needle. The threaded probe protrudes from the sheath, such as by 2-3 mm. The rotating threaded probe is activated to rotate within the inner annular wall. The initial "pass" of the rotating threaded probe is accomplished by withdrawing the introducer needle/sheath/probe linearly back to the position where the introducer/sheath tip is at the level of the opening into the inner annular wall as previously defined. The complex is then advanced back to its position at the opposite inner annular wall as previously defined fluoroscopically. The sheath/probe is kept in its current position while the introducer needle is withdrawn a pre-defined distance, such as 5 mm in one embodiment. The complex is again withdrawn with probe rotating. An additional amount of material is removed, similarly to mowing a lawn. If an additional amount of material is present between the first and second probe withdrawals, the amount of insertional needle withdrawal can be modified to be less than, for example, 5 mm. In successive fashion, the complex is advanced, the introducer needle 40 withdrawn, the rotation of the treaded probe is started, the sheath/probe, and then the introducer segment, is withdrawn until the final sheath/probe withdrawal is accomplished with the introducer needle tip at the level of the insertional inner annular wall. Since the sheath is S shaped, short lengths of sheath protruded from the needle will be arcuate. Incrementally longer segments of exposed sheath assume varying degrees of the S shape. This process very thoroughly evacuates the approximately half of the nucleus that is initially addressed. At this point, the sheath/probe is withdrawn into the introducer needle. The sheath/probe is rotated substantially 180 degrees within the introducer. The process is then repeated in the same fashion on the opposite half of the nucleus. Infusion of a substance, which could be normal saline, via a side portal 32 into the sheath, alternating with suction at portal 34, may be performed at intervals to facilitate removal of the nuclear contents.

Figure 21:
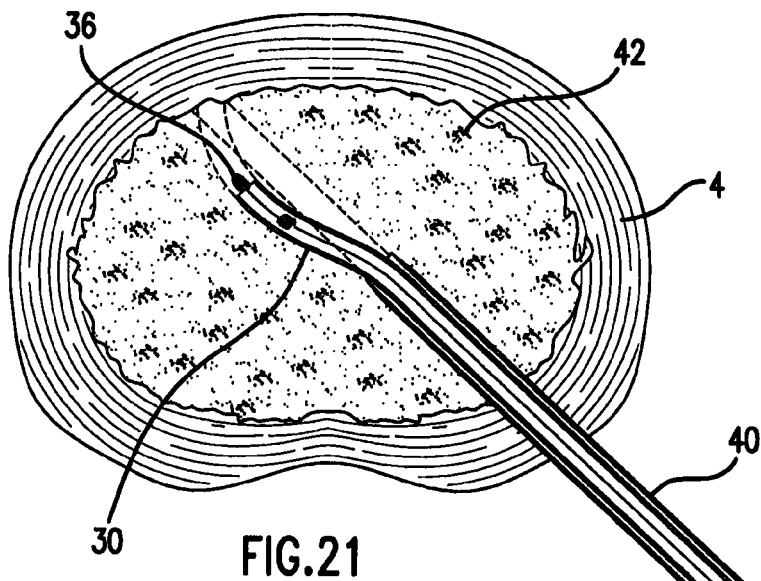
FIG. 21 demonstrates a progressive step in removing material from the disc.
Figure 22A:
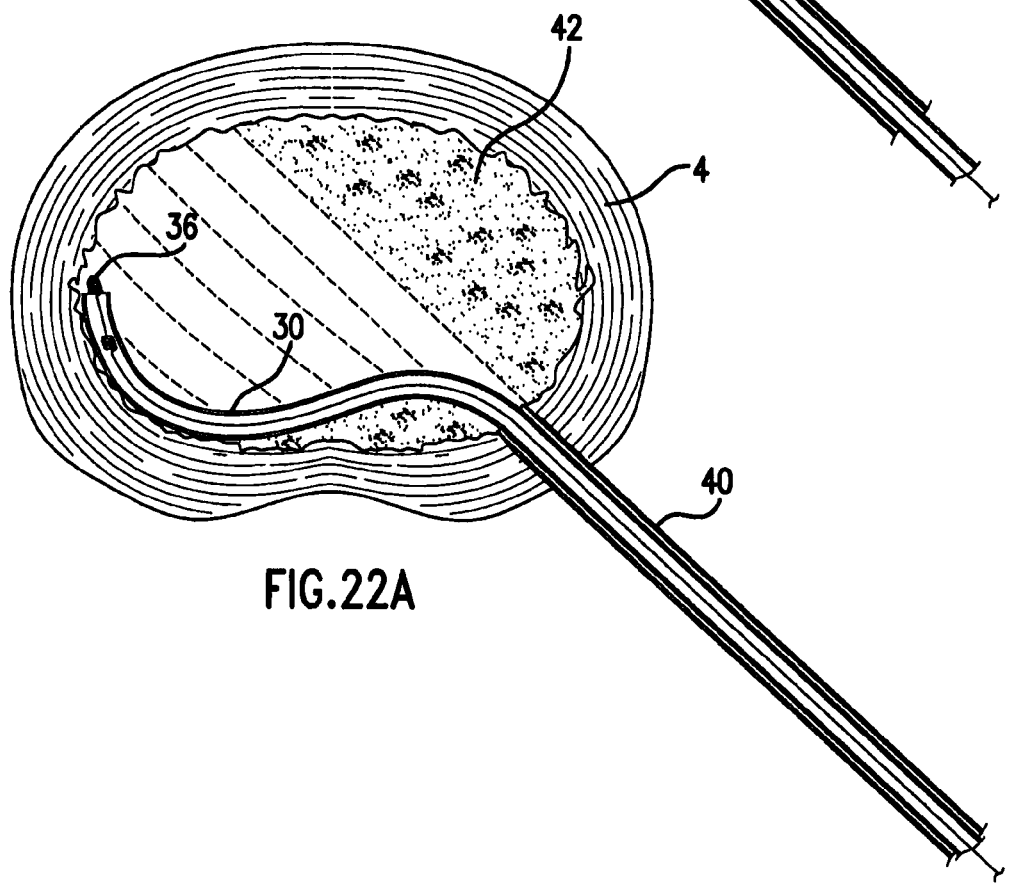
FIG. 22 demonstrates an additional progressive step in removing material from the disc.

The sheath has a pre-formed S shape, and a memory for the S shape. Accordingly, as the rotary cutter is extended from the introducer needle, the sheath will continue to curve slightly, which allows material 42 which is adjacent to the cut taken in FIG. 20 to be removed. FIG. 21. As the rotary cutter cuts material away, lavage/suction are applied through the ports 34 of the introducer needle. One port allows for infusion of a substance (which may be normal saline) into one port. The other port is for suction or other form of removal of material including debris from the disc. By increasing the length of the S shaped sheath from the needle 40, additional passes each take material from the disc, as the cutter is further extended from the sheath. FIG. 22A demonstrates the cutter after the cutter has made six passes, and is beginning a seventh pass. In each pass, the arcuate shape of the sheath as it is extended which allows for progressively removing from the interior of the disc. Shorter segments of the sheath exposed from the introducer needle have an arcuate shape allowing for an infinite number of paths throughout the disc enabling the removal of nuclear material if needed.

Figure 22B:
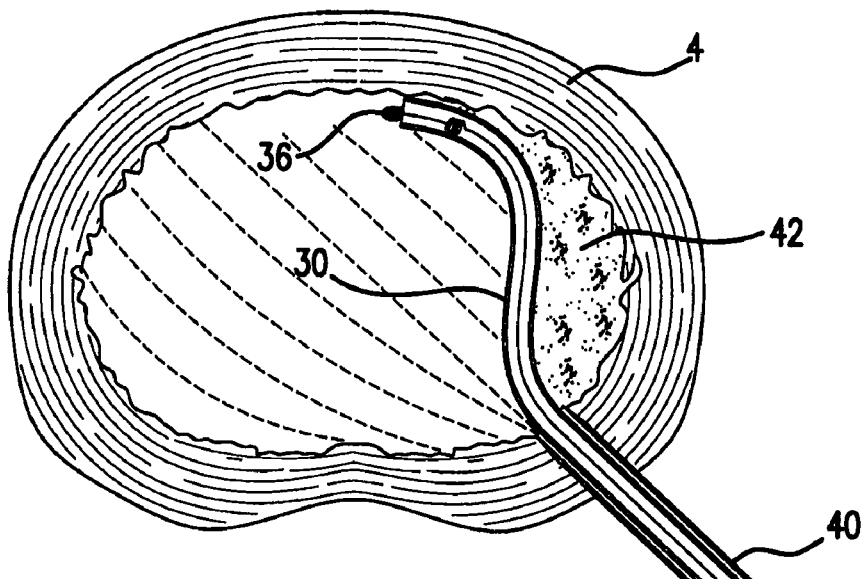
Figure 23:
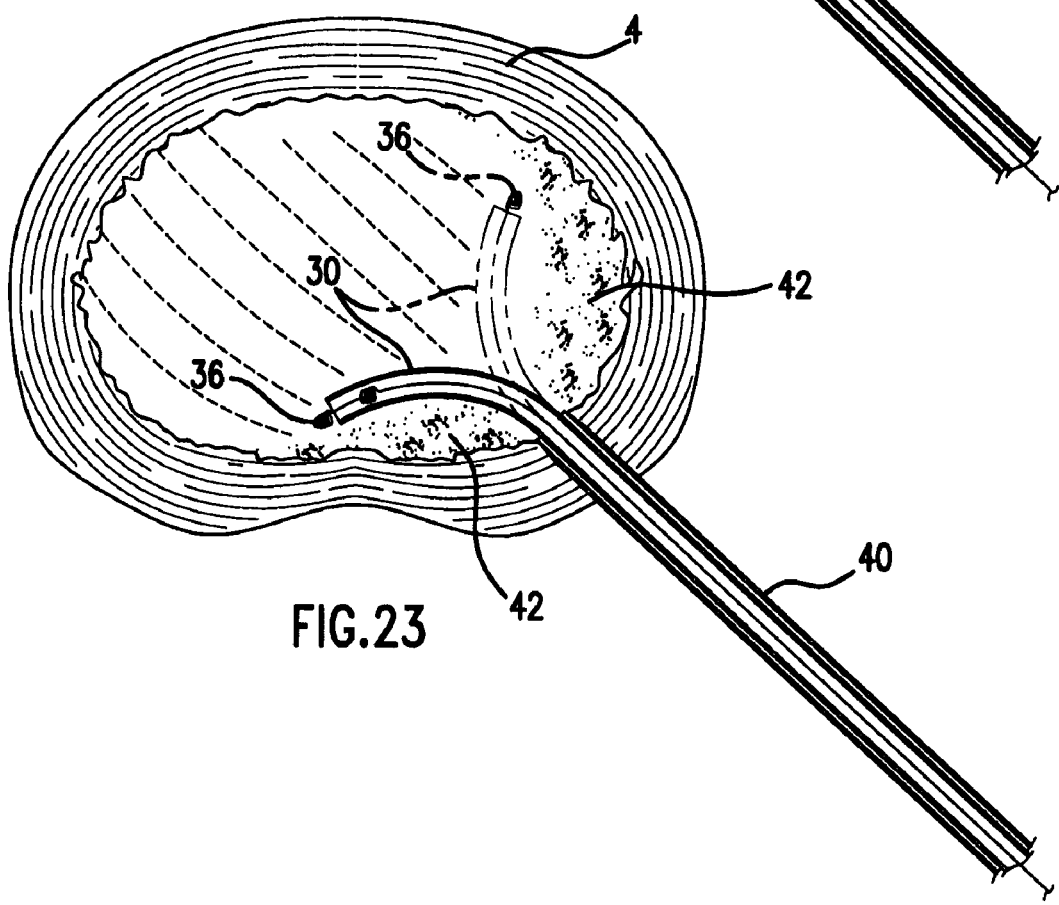
FIG. 23 demonstrates yet an additional step in removing material from the disc.

After the material is removed from one side of the disc, the cutter is retracted into the needle. The cutter and/or the sheath are rotated 180 degrees, so that the S shaped cutter is present on the opposite side of the disc. FIG. 22B. The sheath containing the cutter is extended from the introducer needle on each subsequent pass as needed, until material is removed as desired from the disc as shown in FIG. 23.

Figure 24:
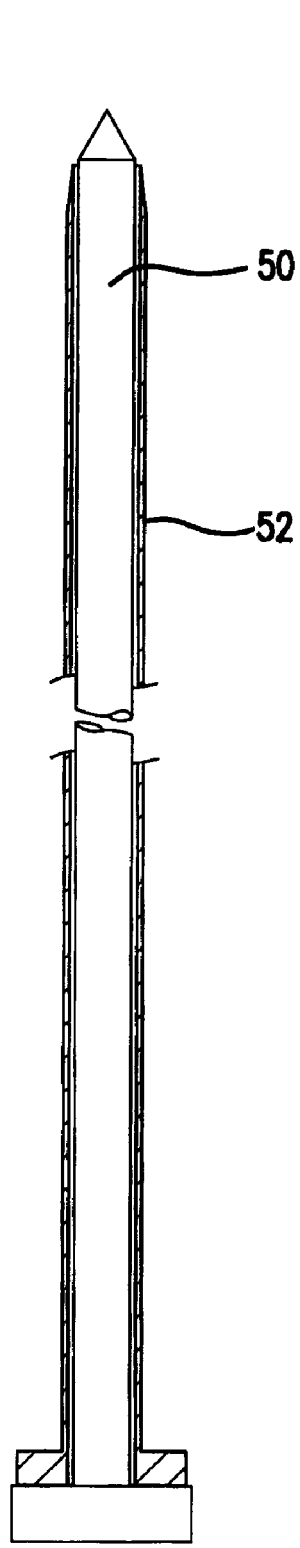
FIG. 24 is a sectioned view of an introducer with a trocar present therein.
Figure 25:
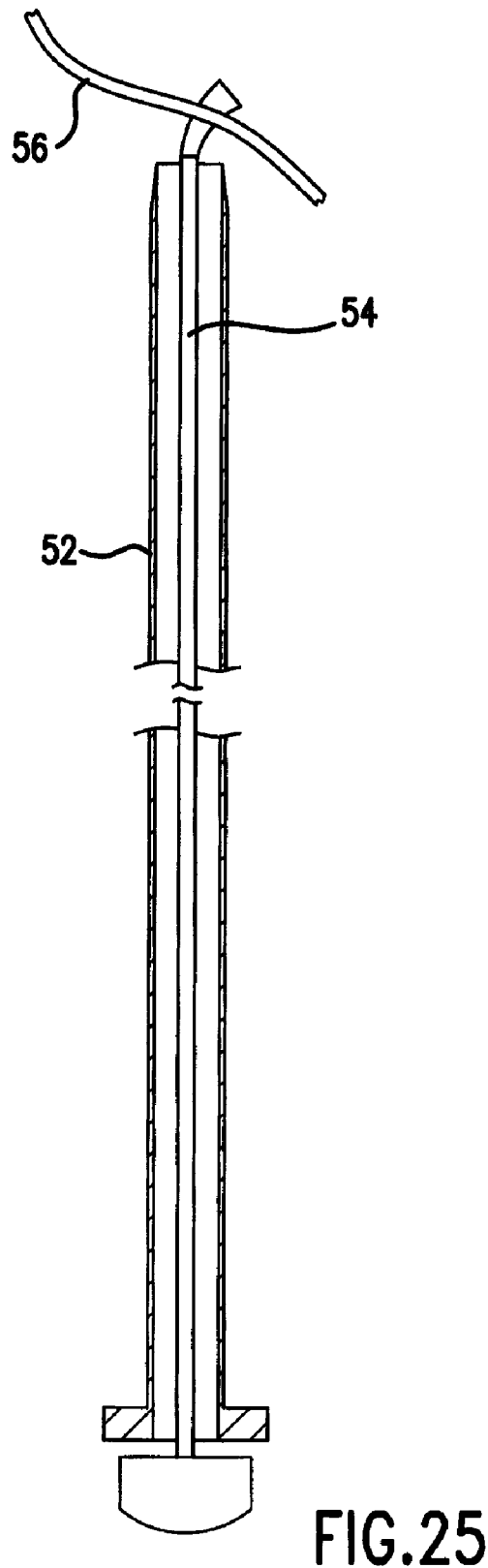
FIG. 25 is a sectioned view of the introducer with a retractor therein.

FIG. 24 shows a trocar 50 that is a present within an introducer 52. The trocar may be a relatively large stylet. FIG. 25 shows a retractor 54 that is present within the introducer. The retractor manipulates the nerve root 56.

Figure 26:
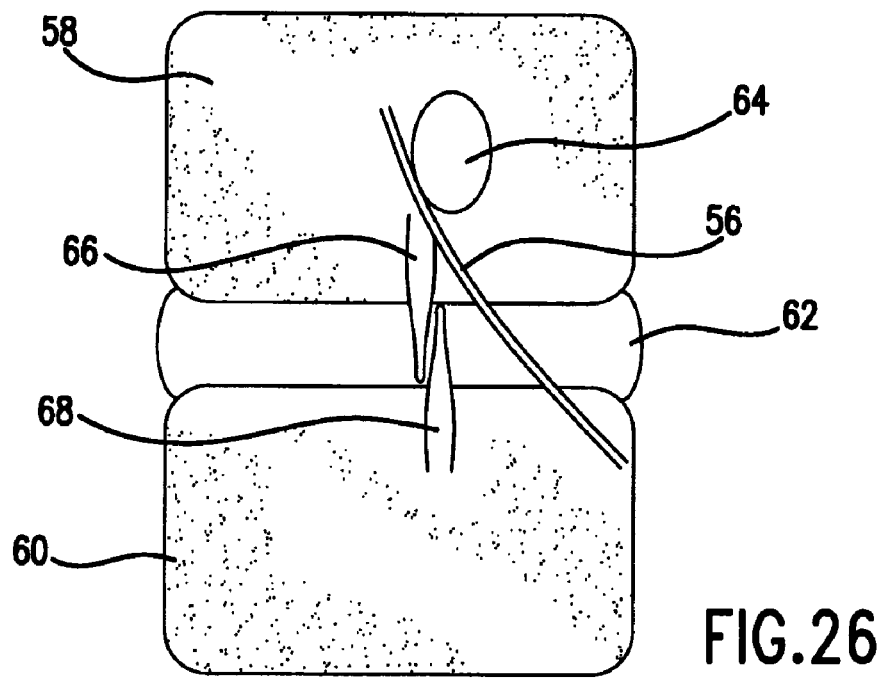
FIG. 26 is an oblique partial view of a mammalian spine.

FIG. 26 shows a vertebra 58 of a mammalian spine, an additional vertebra 60 of a mammalian spine, with an intervertebral disc 62 between the vertebrae. Also shown are a pedicle 64, a superior articular facet 68 and an inferior articular facet 66. The nerve root 56 is shown as traversing the intervertebral disc. As shown, the position of the nerve root interferes with access to the intervertebral disc. FIG. 26 is an oblique view demonstrating what is typically visualized fluoroscopically for intradiscal procedures, except for the nerve root, which does not visualize under fluoroscopy, but whose position is known to an experienced operator.

Figure 27:
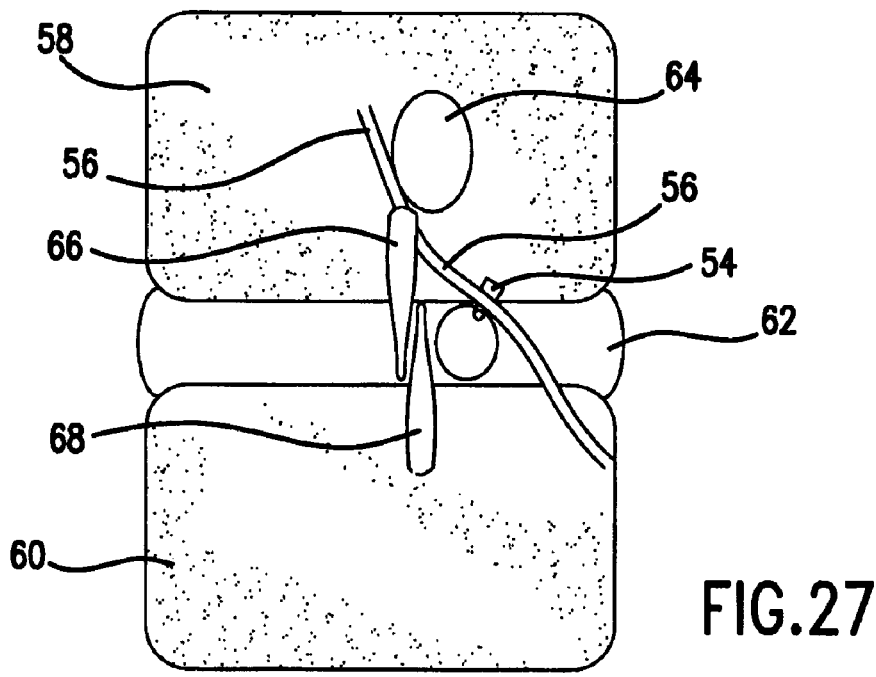
FIG. 27 is an oblique partial view of the mammalian spine with a retractor in position.

The trocar is used to pierce and penetrate skin and other tissue. Upon reaching the nerve root, the trocar is removed and the retractor is inserted. The retractor is used to lift the nerve root over the introducer needle, so that the nerve root is out of the way, and does not interfere with access to the intervertebral disc. FIG. 27.

Once the retractor has repositioned the nerve root over the introducer, the retractor may be removed from the introducer, and the trocar reinserted into the introducer. With the nerve root positioned over the introducer, the nerve root will not be damaged as the trocar and introducer are inserted into the intervertebral disc. The trocar pierces the intervertebral disc for access to the disc with the introducer.

Figure 28:
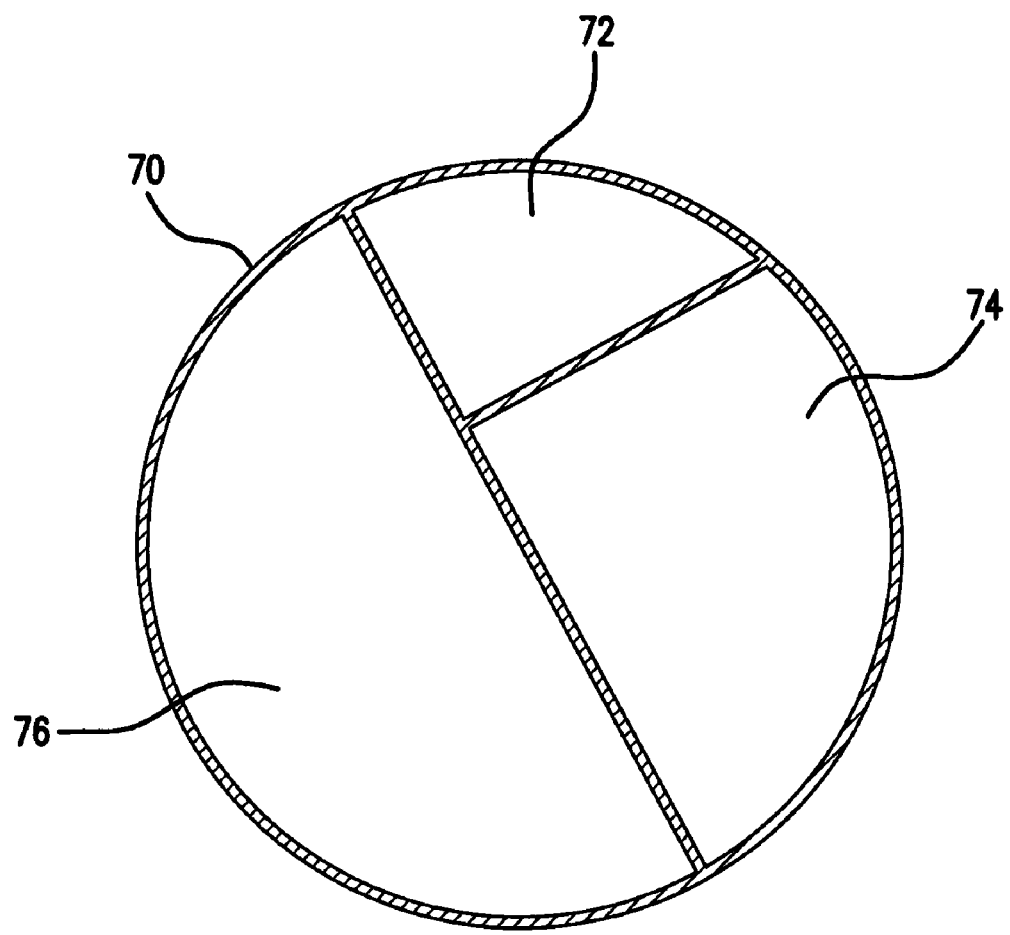
FIG. 28 is a sectioned view of a sheath.

FIG. 28 demonstrates a cross section of a sheath 70 that is used to evacuate a defective disc according to the method described. The sheath has three lumens in the embodiment shown. A first lumen 72 is used as a conduit for a fiber optic cable. A second lumen 74 is provided through which a cutter is delivered to the work site within the intervertebral disc. The cutter could be a laser cutter, or a mechanical cutter, such as a rotary cutter.

A third lumen 76 is relatively larger, and provides a conduit for lavage and suction. Saline or other materials may be introduced to the work site in the disc through the lumen. Tissue that is removed, along with attendant blood and other materials, may be suctioned and evacuated through lumen 76.

Figure 29:
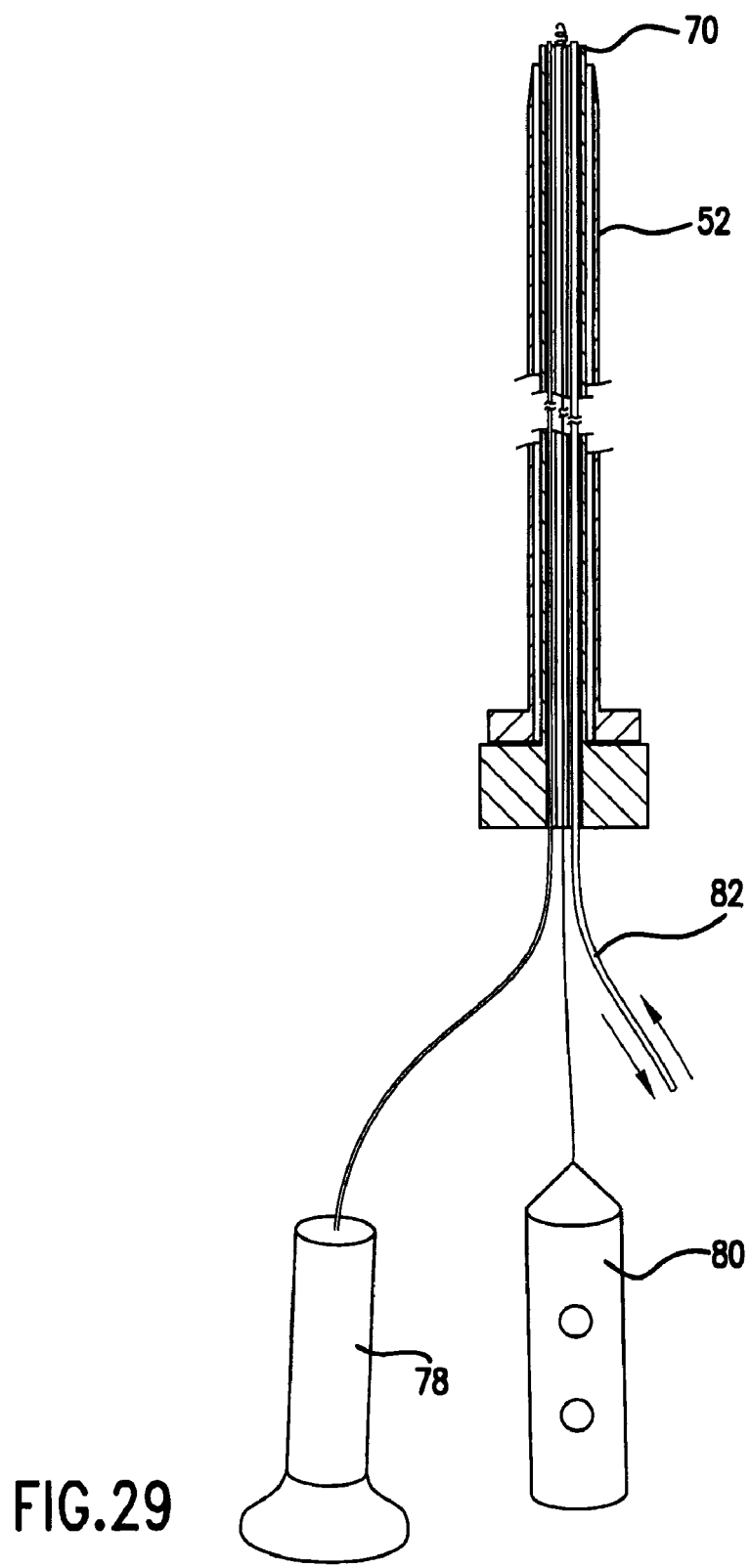
FIG. 29 is a sectioned view of a sheath and introducer with a cutter, fiber optic source and lavage and suction in place.

FIG. 29 shows the fiber optic source 78, cutter 80 and the conduit for lavage and suction 82.

Figure 30:
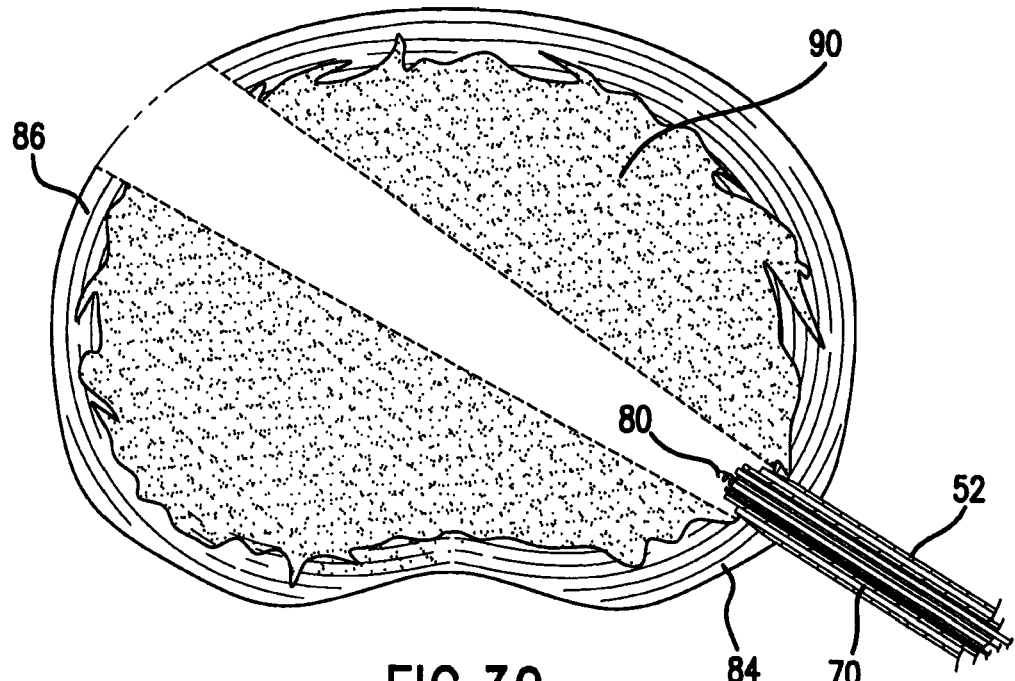
FIG. 30 is plan view of a mammalian intervertebral disc showing a portion of the disc evacuated according to the method of the invention.

The introducer penetrates the wall of the disc as described above. The introducer is shown as having penetrated the lateral posterior wall of the disc 84 in FIG. 30. The sheath is positioned within the disc through the introducer. The sheath is initially positioned so that its forward end extends only slightly beyond the end of the introducer needle. The cutter, the fiber optic and the lavage and suction are actuated, and the entire assembly, along with the introducer needle, are pushed to the opposite wall 86 of the disc, which in this case, is the lateral anterior portion of the disc so that the pulposa of the disc and the disc wall itself are removed, as shown in FIG. 30. Since the materially extended sheath has an S-shape when no pressure is applied to the sheath, there will be a slight curvature of the sheath as it marginally extends from the introducer needle. Accordingly, the cut as shown in FIG. 30 is somewhat conical in shape, rather than being straight, due to the arcuate shape of the sheath when the sheath is advanced slightly from the introducer.

Figure 31:
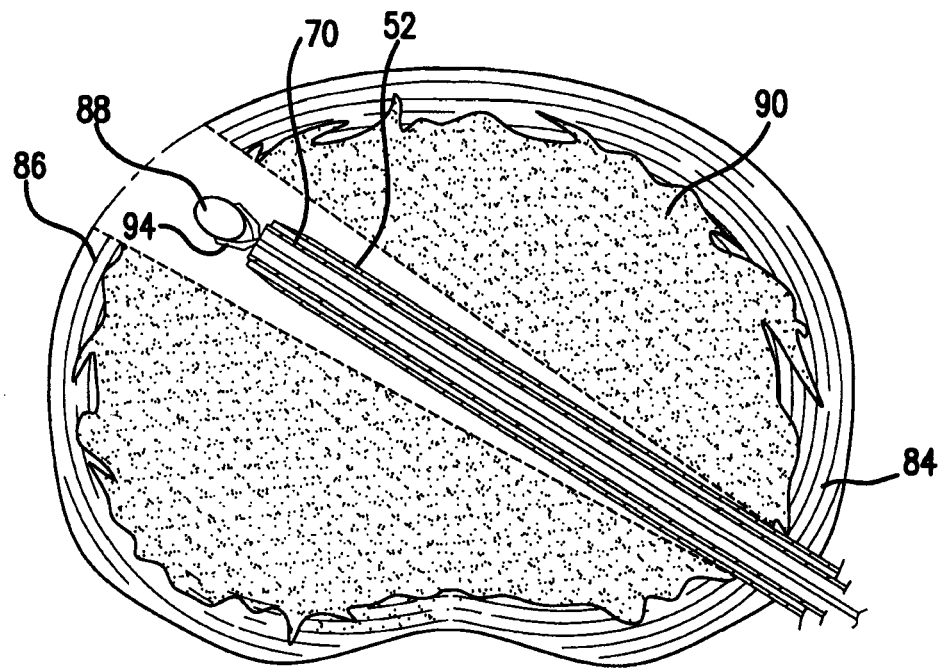
FIG. 31 shows placement of a support member within the intervertebral disc.

The evacuation progresses outwardly. As the intervertebral disc is removed, support must be provided for the adjoining the vertebrae. FIG. 31 shows the cutter removed from the sheath, and a support member or strut 88 placed in position using insertion or placement tool. The support member or strut may be capable of inflation using, for example, saline. Accordingly, the support member or strut may be a balloon or bladder.

Figure 32:
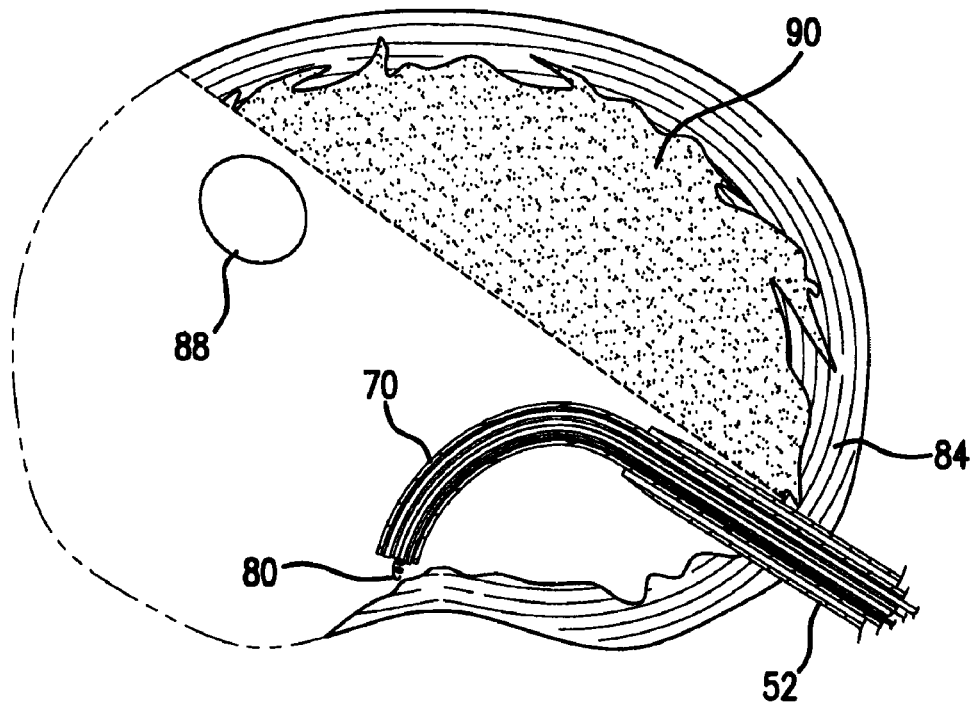
FIG. 32 shows a progressive step of the disc being evacuated according to the method of the invention.
Figure 33:
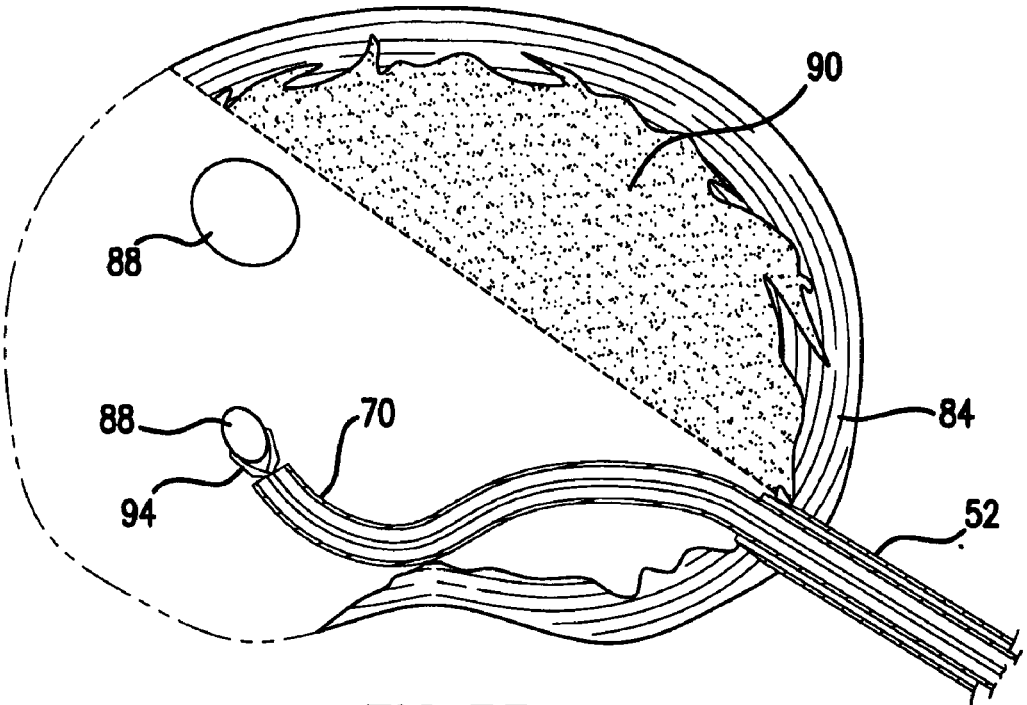
FIG. 33 shows an additional support being positioned within the disc.

The sheath is progressively extended, and progressive cuts are made using the introducer to traverse generally linearly in and out of the disc. As shown in FIG. 32, progressive cuts are made until the disc and associated pulposa 90 are substantially completely removed from one side of the introducer needle. The cutter may be removed from the sheath as required, and the placement tool inserted for placement of the support members or struts within the intervertebral disc.

Figure 34:
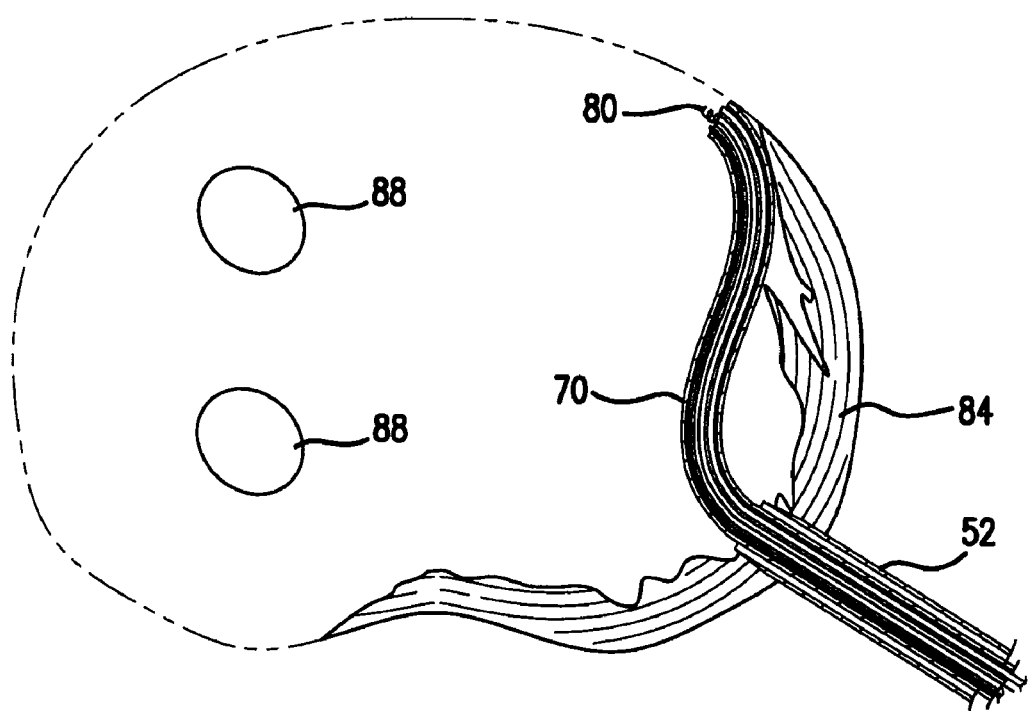
FIG. 34 shows an additional progressive step of the disc being evacuated according to the method of the invention.
Figure 35:
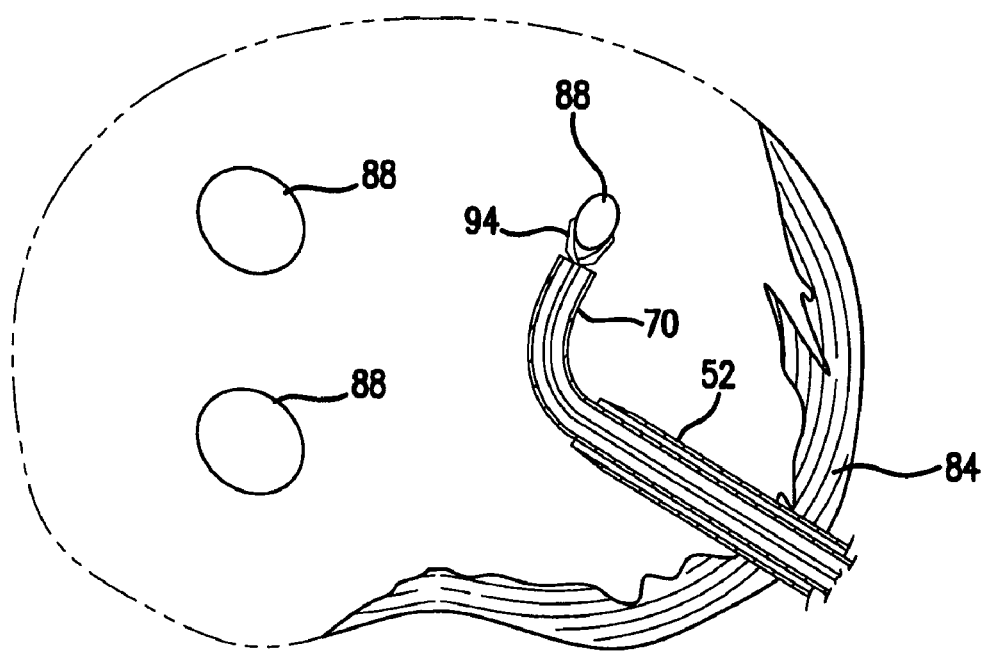
FIG. 35 shows an additional support being positioned within the disc.

After one side of the disc is substantially removed, the sheath, and/or the introducer needle and sheath, are rotated 180 degrees. FIG. 34. The cutter is in position in the sheath. Additional progressive passes are made by steering and advancing the introducer and sheath, individually, or as a unit within the disc, and with the cutter in place. The sheath is progressively extended on each pass, so that the portion of the disc that is further away from the introducer is removed with each progressive pass.

The S-shape of the sheath permits the material of the disc to be removed which is offset to each side of the introducer, even though the introducer is advanced and retracted on what is generally a straight line dictated by the void formed in the disc through which the introducer passes. The S-shape of the sheath allows the cutter to reach progressively laterally as the sheath is progressively extended from the introducer. The sheath of this embodiment, and the catheter shown in FIG. 3 through FIG. 14, and the sheath shown in FIG. 22A through FIG. 23, each have an S-shape when no material pressure is applied to the catheter or sheath. The catheter or sheath in each embodiment of the invention shown herein has a memory property which returns the catheter or sheath to an S-shape when no material pressure is applied to the catheter or sheath. However, when the catheter or sheath is present within the introducer, or in the case of the catheter, within the sheath for the catheter, the S shaped element is reformed to be straight, but regains it S shape as it exits the straight lumen. The sheath is preferred to be straight, and in some embodiments, rigid when used with an S-shaped catheter or tool having shape memory.

Figure 36:
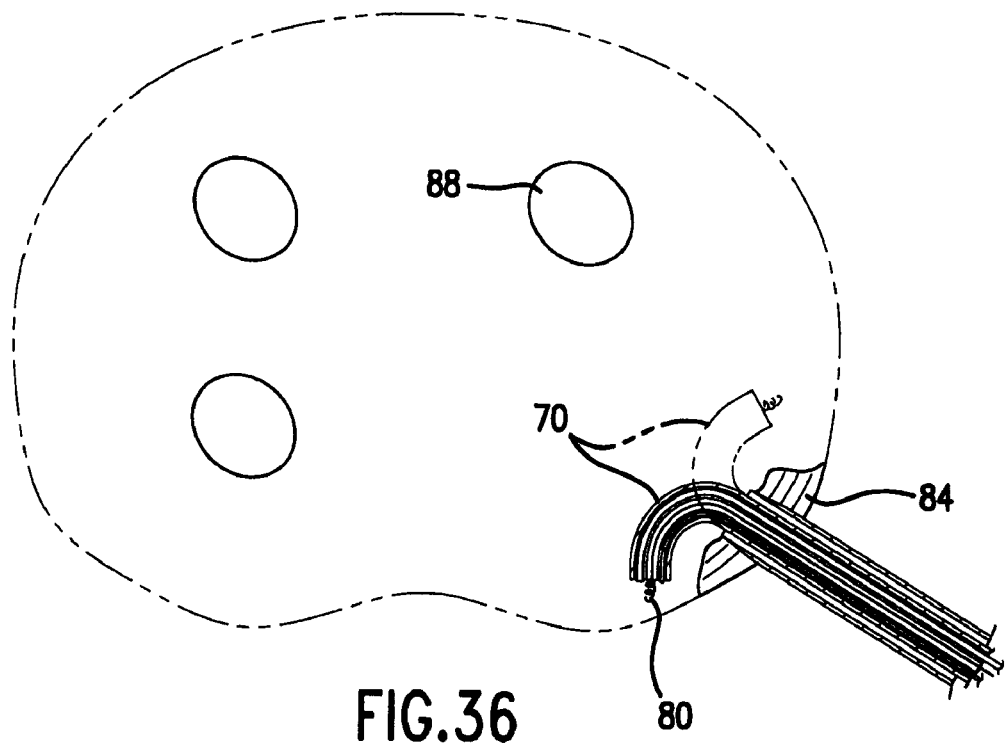
FIG. 36 shows an additional progressive step of the disc being evacuated according to the method of the invention.
Figure 37:
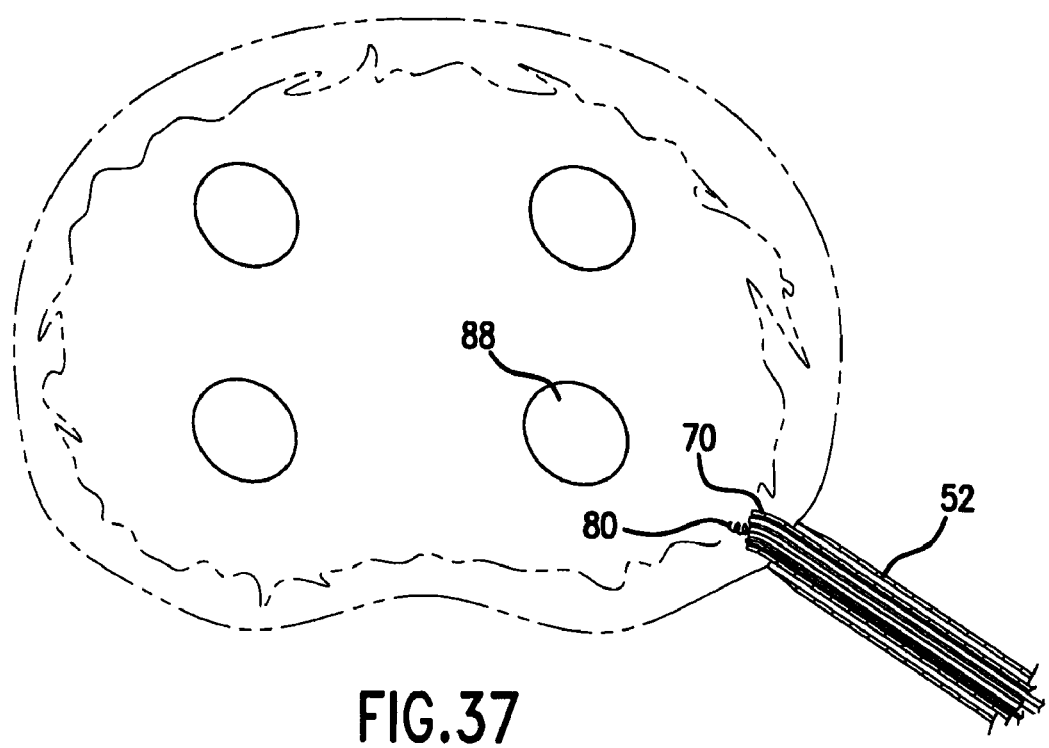
FIG. 37 shows an additional progressive step of the disc being evacuated according to the method of the invention.

Continuing with the process of this preferred embodiment as shown in the drawings, FIG. 36 demonstrates the final cutting away of the disc by slight protrusion of the sheath from the introducer. FIG. 37 uses the cutter with the cutter even more slightly extending from the needle to remove the disc. However, in practice, it may be necessary to remove the entire intervertebral disc. It may be desirable to leave some of the intervertebral disc in place as a support, as long as the targeted defective portion of the intervertebral disc is removed by the method described herein.

The procedures and processes described herein may be, and are preferred to be, performed percutaneously. The procedures and processes may be performed using stab incision or small incision techniques, or techniques wherein an incision of about 2.5 centimeters or less is used to provide access for the introducer, the sheath and/or the tool.

What is claimed is:

1. A device for use in treatment or evacuation of an interior of a mammalian intervertebral disc, comprising:
    a) an introducer for introducing an elongated tool into the interior of the mammalian intervertebral disc, said introducer comprising a guide; and
    b) an elongated tool formed of shape memory material and comprising a preformed S-shape, wherein the S-shape comprises two separate and distinct arcs, and wherein said elongated tool engages said guide, and said elongated tool is transported into the interior of the mammalian intervertebral disc by said guide of said introducer, and said S-shape of said elongated tool is deformable and is deformed by said introducer as said elongated tool is transported along said guide, and said elongated tool regains its preformed S-shape upon exiting said guide of said introducer, wherein the guide and the elongated tool are constructed and arranged so that a distal end of the elongated tool is selectively positioned at different points of the mammalian intervertebral disc by combining selective advancement and retraction of the elongated tool within the interior of the mammalian intervertebral disc with independent selective advancement and retraction of the introducer.

2. A device for use in treatment or evacuation of an interior of a mammalian intervertebral disc as described by claim 1, wherein said guide comprises a lumen, and where said elongated tool is transported into the interior of the mammalian intervertebral disc through said lumen.

3. A device for use in treatment or evacuation of the interior of a mammalian intervertebral disc as described in claim 1, wherein said introducer comprises a lumen, and wherein said guide is a sheath, and wherein said sheath is transported through said lumen of said introducer and into the interior of the mammalian intervertebral disc.

4. A device for use in treatment or evacuation of the interior of a mammalian intervertebral disc as described in claim 1, wherein said elongated tool comprises a deformable locator tip that extends beyond a distal end of said sheath, wherein said deformable locator tip is visible under a fluoroscope.

5. A device for use in treatment or evacuation of the interior of a mammalian intervertebral disc as described in claim 1, wherein said elongated tool comprises a cutter.

6. A device for use in treatment or evacuation of the interior of a mammalian intervertebral disc as described in claim 3, wherein said sheath comprises two lumens that longitudinally traverse a length of said sheath.

7. A device for use in treatment or evacuation of the interior of a mammalian intervertebral disc as described in claim 3, wherein said sheath comprises two lumens that longitudinally traverse a length of said sheath, and wherein material is transported through one of said lumens of said sheath.

8. A device for use in treatment or evacuation of the interior of a mammalian intervertebral disc as described in claim 1, wherein said elongated tool comprises means for separating tissue from said disc.

9. A device for use in treatment or evacuation of the interior of a mammalian intervertebral disc as described in claim 1, wherein said elongated tool comprises radio frequency emitting means.

10. A device for use in treatment or evacuation of the interior of a mammalian intervertebral disc as described in claim 1, wherein said elongated tool comprises heat emitting means.

11. A device for use in treatment or evacuation of the interior of a mammalian intervertebral disc as described in claim 1, wherein said elongated tool comprises forceps.

12. A device for use in treatment or evacuation of the interior of a mammalian intervertebral disc as described in claim 3, wherein said sheath comprises three lumens that longitudinally traverse a length of said sheath.

13. A device for use in treatment or evacuation of the interior of a mammalian intervertebral disc as described in claim 3, wherein said sheath comprises three lumens that longitudinally traverse a length of said sheath, and wherein materials are delivered to the interior of the mammalian intervertebral disc through one of the lumens, and materials are withdrawn from the interior of the mammalian intervertebral disc through one of the lumens.

14. A device for use in treatment or evacuation of the interior of a mammalian intervertebral disc as described in claim 1, wherein said elongated tool comprises fiber optic cable.

15. A device for use in treatment or evacuation of the interior of a mammalian intervertebral disc as described in claim 1, wherein said elongated tool comprises means for removing tissue from the interior of the mammalian intervertebral disc.

16. A device for use in treatment or evacuation of the interior of a mammalian intervertebral disc as described in claim 3, wherein said sheath opens at a distal end of said sheath, and wherein said elongated tool extends from and beyond said distal end of said sheath.

17. A device for use in treatment or evacuation of the interior of a mammalian intervertebral disc as described in claim 1, wherein said introducer is substantially straight.

18. A device for use in treatment or evacuation of the interior of a mammalian intervertebral disc as described in claim 3, wherein said introducer is substantially straight and forms a portion of said sheath as straight as said sheath is transported by said introducer.

19. A device for use in treatment or evacuation of the interior of a mammalian intervertebral disc as described in claim 1, wherein said introducer comprises a substantially straight lumen that forms said elongated tool as straight as said elongated tool is transported by said introducer.

20. A device for use in treatment or evacuation of the interior of a mammalian intervertebral disc as described in claim 1, wherein said elongated tool therapeutically treats the interior of the mammalian intervertebral disc.

21. A device for use in treatment or evacuation of the interior of a mammalian intervertebral disc as described in claim 1, wherein said elongated tool minimizes contents of the interior of the mammalian intervertebral disc.

22. A device for use in treatment or evacuation of the interior of a mammalian intervertebral disc as described in claim 3, wherein said sheath comprises a side portal.

23. A device for use in treatment or evacuation of the interior of a mammalian intervertebral disc as described in claim 1, wherein said elongated tool comprises means for positioning spacers in the interior of the mammalian intervertebral disc.

24. A device for use in treatment or evacuation of the interior of a mammalian intervertebral disc as described in claim 23, further comprising spacers for positioning in the interior of the mammalian intervertebral disc.

25. A device for use in treatment or evacuation of the interior of a mammalian intervertebral disc as described in claim 1, wherein the elongated tool is constructed and arranged to reach substantially all surfaces in the interior of the mammalian intervertebral disc from a posterior or postero lateral approach to the disc by combining selective advancement and retraction of the elongated tool within the interior of the mammalian intervertebral disc with independent selective advancement and retraction of the introducer.

26. A device for use in treatment or evacuation of an interior of a mammalian intervertebral disc as described in claim 1, wherein said elongated tool is constructed and arranged to be rotatable relative to said introducer.

27. A device for use in treatment or evacuation of an interior of a mammalian intervertebral disc as described by claim 1, wherein said elongated tool is constructed and arranged to be rotatable relative to said introducer to an inverted position.

28. A device for use in treatment or evacuation of an interior of a mammalian intervertebral disc as described in claim 1, wherein the distal end of the elongated tool is formable to an arcuate shape of a curved interior surface of the mammalian intervertebral disc and the arcuate shape of the distal end of the elongated tool is positioned at the curved interior surface of the mammalian intervertebral disc by combining selective advancement and retraction of the elongated tool within the interior of the mammalian intervertebral disc with independent selective advancement and retraction of the introducer.

29. A device for use in treatment or evacuation of an interior of a mammalian intervertebral disc, comprising:
   a) an introducer for introducing an elongated tool into the interior of the mammalian intervertebral disc, said introducer comprising a guide; and
   b) an elongated tool formed of shape memory material and comprising a preformed S-shape, and wherein said elongated tool engages said guide, and said elongated tool is transported into the interior of the mammalian intervertebral disc by said guide of said introducer, and said S-shape of said elongated tool is deformable and is deformed by said introducer as said elongated tool is transported along said guide, and said elongated tool regains its preformed S-shape upon exiting said guide of said introducer, wherein the guide and the elongated tool are constructed and arranged so that a distal end of the elongated tool is positionable on all interior surfaces of the mammalian intervertebral disc by combining selective advancement and retraction of the elongated tool within the interior of the mammalian intervertebral disc with independent selective advancement and retraction of the introducer.

30. A device for use in treatment or evacuation of an interior of a mammalian intervertebral disc as described by claim 29, wherein said guide comprises a lumen, and where said elongated tool is transported into the interior of the mammalian intervertebral disc through said lumen.

31. A device for use in treatment or evacuation of the interior of a mammalian intervertebral disc as described in claim 29, wherein said introducer comprises a lumen, and wherein said guide is a sheath, and wherein said sheath is transported through said lumen of said introducer and into the interior of the mammalian intervertebral disc.

32. A device for use in treatment or evacuation of the interior of a mammalian intervertebral disc as described in claim 29, wherein said elongated tool comprises a deformable locator tip that extends beyond a distal end of said sheath, wherein said deformable locator tip is visible under a fluoroscope.

33. A device for use in treatment or evacuation of the interior of a mammalian intervertebral disc as described in claim 29, wherein said elongated tool comprises a cutter.

34. A device for use in treatment or evacuation of the interior of a mammalian intervertebral disc as described in claim 31, wherein said sheath comprises two lumens that longitudinally traverse a length of said sheath.

35. A device for use in treatment or evacuation of the interior of a mammalian intervertebral disc as described in claim 31, wherein said sheath comprises two lumens that longitudinally traverse a length of said sheath, and wherein material is transported through one of said lumens of said sheath.

36. A device for use in treatment or evacuation of the interior of a mammalian intervertebral disc as described in claim 29, wherein said elongated tool comprises means for separating tissue from said disc.

37. A device for use in treatment or evacuation of the interior of a mammalian intervertebral disc as described in claim 29, wherein said elongated tool comprises radio frequency emitting means.

38. A device for use in treatment or evacuation of the interior of a mammalian intervertebral disc as described in claim 29, wherein said elongated tool comprises heat emitting means.

39. A device for use in treatment or evacuation of the interior of a mammalian intervertebral disc as described in claim 31, wherein said elongated tool comprises forceps.

40. A device for use in treatment or evacuation of the interior of a mammalian intervertebral disc as described in claim 31, wherein said sheath comprises three lumens that longitudinally traverse a length of said sheath.

41. A device for use in treatment or evacuation of the interior of a mammalian intervertebral disc as described in claim 31, wherein said sheath comprises three lumens that longitudinally traverse a length of said sheath, and wherein materials are delivered to the interior of the mammalian intervertebral disc through one of the lumens, and materials are withdrawn from the interior of the mammalian intervertebral disc through one of the lumens.

42. A device for use in treatment or evacuation of the interior of a mammalian intervertebral disc as described in claim 29, wherein said elongated tool comprises fiber optic cable.

43. A device for use in treatment or evacuation of the interior of a mammalian intervertebral disc as described in claim 29, wherein said elongated tool comprises means for removing tissue from the interior of the mammalian intervertebral disc.

44. A device for use in treatment or evacuation of the interior of a mammalian intervertebral disc as described in claim 31, wherein said sheath opens at a distal end of said sheath, and wherein said elongated tool extends from and beyond said distal end of said sheath.

45. A device for use in treatment or evacuation of the interior of a mammalian intervertebral disc as described in claim 29, wherein said introducer is substantially straight.

46. A device for use in treatment or evacuation of the interior of a mammalian intervertebral disc as described in claim 31, wherein said introducer is substantially straight and forms a portion of said sheath as straight as said sheath is transported by said introducer.

47. A device for use in treatment or evacuation of the interior of a mammalian intervertebral disc as described in claim 29, wherein said introducer comprises a substantially straight lumen that forms said elongated tool as straight as said elongated tool is transported by said introducer.

48. A device for use in treatment or evacuation of the interior of a mammalian intervertebral disc as described in claim 29, wherein said elongated tool therapeutically treats the interior of the mammalian intervertebral disc.

49. A device for use in treatment or evacuation of the interior of a mammalian intervertebral disc as described in claim 29, wherein said elongated tool minimizes contents of the interior of the mammalian intervertebral disc.

50. A device for use in treatment or evacuation of the interior of a mammalian intervertebral disc as described in claim 31, wherein said sheath comprises a side portal.

51. A device for use in treatment or evacuation of the interior of a mammalian intervertebral disc as described in claim 29, wherein said elongated tool comprises means for positioning spacers in the interior of the mammalian intervertebral disc.

52. A device for use in treatment or evacuation of the interior of a mammalian intervertebral disc as described in claim 51, further comprising spacers for positioning in the interior of the mammalian intervertebral disc.

53. A device for use in treatment or evacuation of the interior of a mammalian intervertebral disc as described in claim 29, wherein the S-shape of the elongated tool formed of shape memory material comprises two separate and distinct arcs.

54. A device for use in treatment or evacuation of an interior of a mammalian intervertebral disc as described in claim 29, wherein said elongated tool is constructed and arranged to be rotatable relative to said introducer.

55. A device for use in treatment or evacuation of an interior of a mammalian intervertebral disc as described by claim 29, wherein said elongated tool is constructed and arranged to be rotatable relative to said introducer to an inverted position.

56. A device for use in treatment or evacuation of an interior of a mammalian intervertebral disc as described in claim 29, wherein the distal end of the elongated tool is formable to an arcuate shape of a curved interior surface of the mammalian intervertebral disc and the arcuate shape of the distal end of the elongated tool is positioned at the curved interior surface of the mammalian intervertebral disc by combining selective advancement and retraction of the elongated tool within the interior of the mammalian intervertebral disc with independent selective advancement and retraction of the introducer.

* * * * *

UNITED STATES PATENT AND TRADEMARK OFFICE
CERTIFICATE OF CORRECTION

PATENT NO.        : 8,308,690 B2                              Page 1 of 1
APPLICATION NO.   : 13/042984
DATED             : November 13, 2012
INVENTOR(S)       : Forrest It is certified that error appears in the above-identified patent and that said Letters Patent is hereby corrected as shown below:

On the title page item [60] and in the specification column 1 lines 5-19,

INSERT

--CON of S.N. 11/972,815 filed 01/11/2008 now U.S. Patent 7,905,863
which is a CON of S.N. 11/112,475 filed 04/23/2005
now U.S. Patent 7,322,962 which claims benefit of 60/564,838 filed 04/23/2004
and claims benefit of 60/572,930 filed 05/20/2004
and claims benefit of 60/586,627 filed 07/09/2004
and claims benefit of 60/588,582 filed 07/16/2004
and claims benefit of 60/588,587 filed 07/16/2004--

Signed and Sealed this
Twenty-sixth Day of January, 2016

Michelle K. Lee
*Director of the United States Patent and Trademark Office*